(12) United States Patent
Ambati

(10) Patent No.: US 9,707,235 B1
(45) Date of Patent: *Jul. 18, 2017

(54) PROTECTION OF CELLS FROM DEGENERATION AND TREATMENT OF GEOGRAPHIC ATROPHY

(71) Applicant: University of Kentucky Research Foundation, Lexington, KY (US)

(72) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 144 days.

This patent is subject to a terminal disclaimer.

(21) Appl. No.: 13/740,828

(22) Filed: Jan. 14, 2013

Related U.S. Application Data

(60) Provisional application No. 61/586,427, filed on Jan. 13, 2012.

(51) Int. Cl.
*A61K 31/5377* (2006.01)

(52) U.S. Cl.
CPC ................................ *A61K 31/5377* (2013.01)

(58) Field of Classification Search
None
See application file for complete search history.

(56) References Cited

U.S. PATENT DOCUMENTS

| 2006/0116419 A1* | 6/2006 | Callahan .............. A61K 31/381 514/447 |
| 2010/0092486 A1* | 4/2010 | Kandimalla et al. ...... 424/158.1 |
| 2010/0136097 A1* | 6/2010 | Hyde et al. ................... 424/450 |

FOREIGN PATENT DOCUMENTS

| WO | WO 2009015107 A1 * | 1/2009 |
| WO | WO 2012021773 A1 * | 2/2012 |

OTHER PUBLICATIONS

Ding et al. (2009) Molecular pathology of age-related macular degeneration. Progress in Retinal and Eye Research, 28:1-18.*
Doyle et al. (2012) NLRP3 has a protective role in age-related macular degeneration through the induction of IL-18 by drusen components. Nature Medicine, 18(5):791-799.*
Hirano et al. (2014) IL-18 is not therapeutic for neovascular age-related macular degeneration. Nature Medicine, 20(12):1372-1375.*
Ijima et al. (2014) Interleukin-18 Induces Retinal Pigment Epithelium Degeneration in Mice. Investigative Ophthalmology & Visual Science, 55(10):6673-6678.*
Chen et al. (2012) Protective inflammasome activation in AMD. Nature Medicine, 18(5), 658-660.*
Doyle et al. (2014) Reply to IL-18 is not therapeutic for neovascular age-related macular degeneration. Nature Medicine, 20(12):1376-1377.*
Sobrin et al. (2011) ARMS2/HTRA1 Locus Can Confer Differential Susceptibility to the Advanced Subtypes of Age-Related Macular Degeneration. Journal of Ophthalmology, 151:345-352.*
Kaneko et al. (2011) DICER1 deficit induces Alu RNA toxicity in age-related macular degeneration. Nature, 471:325-330.*
Schroder et al. (2010) The Inflammasomes. Cell, 140:821-832.*
Bleicher et al. (2003) Hit and Lead Generation: Beyond High-Throughput Screening. Nature Reviews Drug Discovery, 2:369-378.*
Novick et al. (1999) Interleukin-18 Binding Protein: A Novel Modulator of the Th1 Cytokine Response. Immunity, 10(1):127-136.*
Plater-Zyberk et al. (2001) Therapeutic effect of neutralizing endogenous IL-18 activity in the collagen-induced model of arthritis. The Journal of Clinical Investigation, 108(12):1825-1832.*
Juliana et al. (2008) Anti-inflammatory Compounds Parthenolide and Bay 11-7082 Are Direct Inhibitors of the Inflammasome. The Journal of Biological Chemistry, 285(13):9792-9802.*
Franchi et al. (2009) The inflammasome: a caspase-1-activation platform that regulates immune responses and disease pathogenesis. Nature Immunology, 10(3):241-247.*
Ijima et al., "Interleukin-18 Induces Retinal Pigment Epithelium Degeneration in Mice," Invest Ophtalmol Vis Sci, 2014, 18;55(10), pp. 6673-6678, doi: 10.1167/iovs.14-15367.
Hirano et al., "IL 18 is not therapeutic for neovascular age-related macular degeneration", Nature Medicine, doi:10.1038/nm.3671.
Hirano et al., "IL 18 is not therapeutic for neovascular age-related macular degeneration", Nature Medicine, 2014, vol. 20, No. 12, pp. 1372-1375.
Ambati, J., Ambati, B.K., Yoo, S.H., Ianchulev, S., and Adamis, A.P. (2003). Age-related macular degeneration: etiology, pathogenesis, and therapeutic strategies. Surv Ophthalmol 48, 257-293.
Schroder, K., and Tschopp, J. (2010). The inflammasomes. Cell 140, 821-832.
Adachi, O., Kawai, T., Takeda, K., Matsumoto, M., Tsutsui, H., Sakagami, M., Nakanishi, K., and Akira, S. (1998). Targeted disruption of the MyD88 gene results in loss of IL-1-and IL-18-mediated function. Immunity 9, 143-150.
Bauernfeind, F., Bartok, E., Rieger, A., Franchi, L., Nunez, G., and Hornung, V. (2011). Cutting edge: reactive oxygen species inhibitors block priming, but not activation, of the NLRP3 inflammasome. J Immunol 187, 613-617.
Ohtsuki, T., Micallef, M.J., Kohno, K., Tanimoto, T., Ikeda, M., and Kurimoto, M. (1997). Interleukin 18 enhances Fas ligand expression and induces apoptosis in Fas-expressing human myelomonocytic KG-1 cells. Anticancer Res 17, 3253-3258.
Suzuki, N., Chen, N.J., Millar, D.G., Suzuki, S., Horacek, T., Hara, H., Bouchard, D., Nakanishi, K., Penninger, J.M.,. Ohashi, P.S., et al. (2003). IL-1 receptor-associated kinase 4 is essential for IL-18-mediated NK and Th1 cell responses. J Immunol 170, 4031-4035.
Verhoef, P.A., Kertesy, S.B., Lundberg, K., Kahlenberg, J.M., and Dubyak, G.R. (2005). Inhibitory effects of chloride on the activation of caspase-1, IL-1beta secretion, and cytolysis by the P2X7 receptor. J Immunol 175, 7623-7634.

(Continued)

*Primary Examiner* — Neil P Hammell
(74) *Attorney, Agent, or Firm* — Stites & Harbison PLLC; Mandy Wilson Decker; Sean Ritchie

(57) ABSTRACT

Therapeutic uses P2X$_7$ inhibition and inhibition of IRAK1 and/or IRAK4, methods protecting a cell, and screening methods for identifying inhibitors are described herein.

2 Claims, 24 Drawing Sheets

(56) References Cited

OTHER PUBLICATIONS

Lamkanfi, M., Mueller, J.L., Vitari, A.C., Misaghi, S., Fedorova, A., Deshayes, K., Lee, W.P., Hoffman, H.M., and Dixit, V.M. (2009). Glyburide inhibits the Cryopyrin/Nalp3 inflammasome. J Cell Biol 187, 61-70.
Suzuki, N., Suzuki, S., Duncan, G.S., Millar, D.G., Wada, T., Mirtsos, C., Takada, H., Wakeham, A., Itie, A., Li, S., et al. (2002). Severe impairment of interleukin-1 and Toll-like receptor signalling in mice lacking IRAK-4. Nature 416, 750-756.
Mariathasan, S., Weiss, D.S., Newton, K., McBride, J., O'Rourke, K., Roose-Girma, M., Lee, W.P., Weinrauch, Y., Monack, D.M., and Dixit, V.M. (2006). Cryopyrin activates the inflammasome in response to toxins and ATP. Nature 440, 228-232.
Kaneko, H., Dridi, S., Tarallo, V., Gelfand, B.D., Fowler, B.J., Cho, W.G., Kleinman, M.E., Ponicsan, S.L., Hauswirth, W.W., Chiodo, V.A., et al. (2011). DICER1 deficit induces Alu RNA toxicity in age-related macular degeration Nature 471, 325-330.
Bauernfeind, F., et al., Reactive oxygen species inhibitors block priming, but not activation of the NLRP3 inflammasome; J Immunol. Jul. 15, 2011; 187(2): 613-617.
Muzio, M., Ni, J., Feng, P., and Dixit, V.M. (1997). IRAK (Pelle) family member IRAK-2 and MyD88 as proximal mediators of IL-1 signaling. Science 278, 1612-1615.
Brown DM, Kaiser PK, Michels M, et al. Ranibizumab versus verteporfin for neovascular age-related macular degeneration. N Engl J Med 2006;355:1432-44.
Grisanti, et al., The role of vascular endothelial growth factor and other endogenous interplayers in age-related macular degeneration, Progress in Retinal and Eye Research 27 (2008) 372-390.
Hartzell, et al., Looking Chloride Channels Straight in the Eye: Bestrophins, Lipofuscinosis, and Retinal Degeneration, Physiology, 2005, 20: pp. 292-302.
Jaffe, et al., Randomized Trial to Evaluate Tandospirone in Geographic Atrophy Secondary to Age-Related Macular Degeneration: The GATE Study; 2015 The Authors. Published by Elsevier Inc., pp. 1-9.
Rosenfeld PJ, Brown DM, Heier JS, et al. Ranibizumab for neovascular age-related macular degeneration. N Engl J Med 2006;355:1419-31.
Rosenfeld, et al., Ranibizumab for Neovascular Age-Related Macular Degeneration, N Engl J Med 2006;355:1419-31.
Folk & Wilkinson. Protect Your Sight: How to Save Your Vision in the Epidemic of Age-Related Macular Degeneration. F.E.P. International. 2006, p. 126.
Stone & Sheffield. The Molecular Genetic Approach to Macular Degeneration. In Molecular Genetics of Inherited Eye Disorders. Edited by A.F. Wright. CRC Press. 1994, p. 173.
Stone & Sheffield. The Molecular Genetic Approach to Macular Degeneration. In Molecular Genetics of Inherited Eye Disorders. Edited by A.F. Wright. CRC Press. 1994, p. 176.
Yehoshua et al. Systemic Complement Inhibition with Eculizumab for Geographic Atrophy in Age-Related Macular Degeneration. The Complete Study. Ophthalmology 2014;121:693-701.
Zhu et al. What determines the switch between atrophic and neovascular forms of age related macular degeneration?—The role of BMP4 induced senescence. Aging 2009; 1 (8):740-5.
Apte & Rajagopal. In The New Visual Neurosciences. Edited by J.S. Werner & L. Chalupa. MIT Press. 2013, p. 1515.
Basic and Clinical Science Course, Section 12: Retina and Vitreous. American Academy of Ophthalmology. San Francisco, 2013-2014, p. 55.
Basic and Clinical Science Course, Section 12: Retina and Vitreous. American Academy of Ophthalmology. San Francisco, 2013-2014, p. 57.
Basic and Clinical Science Course, Section 12: Retina and Vitreous. American Academy of Ophthalmology. San Francisco, 2013-2014, p. 63.
Loiarro, et al., Peptide-mediated Interference of TIR Domain Dimerization in MyD88 Inhibits Interleukin-1-dependent Activation of NF-B, The Journal of Biological Chemistry vol. 280, No. 16, Issue of Apr. 22, 2005, pp. 15809-15814.
Loiarro, et al., Pivotal Advance: Inhibition of MyD88 dimerization and recruitment of IRAK1 and IRAK4 by a novel peptidomimetic compound, Journal of Leukocyte Biology vol. 82, Oct. 2007, pp. 801-810.
Van Tassell, et al., Pharmacologic Inhibition of Myeloid Differentiation Factor 88 (MyD88) Prevents Left Ventricular Dilation and Hypertrophy After Experimental Acute Myocardial Infarction in the Mouse, Journal of Cardiovascular Pharmacology: Apr. 2010—vol. 55—Issue 4—pp. 385-390 (Abstract).
Bartfal, et al., A low molecular weight mimic of the Toll/IL-1 receptorresistance domain inhibits IL-1 receptor-mediated responses, PNAS, Jun. 24, 2003, vol. 100, No. 13, 7971-7976.
Kissner, et al., A Small Molecule That Mimics the BB-loop in the Toll Interleukin-1 (IL-1) Receptor Domain of MyD88 Attenuates *Staphylococcal* Enterotoxin B-induced Pro-inflammatory Cytokine Production and Toxicity in Mice, The Journal of Biological Chemistry, Sep. 9, 2011, vol. 286, No. 36, pp. 31385-31396.
Li, et al., Nicotine Reduces TNF-α Expression Through a α7 nAChR/MyD88/NF-κB Pathway in HBE16 Airway Epithelial Cells, Cell Physiol Biochem 2011;27:605-612.
Chuang, et al., Toll-like receptor 2-mediated sequential activation of MyD88 and MAPKs contributes to lipopolysaccharide-induced sp-a gene expression in human alveolar epithelial cells, Immunobiology, vol. 216, Issue 6, Jun. 2011, pp. 707-714.
Coll, et al. A small molecule inhibitior of the NLRP3 inflammasome is a potential therapeutic for inflammatory diseases, Nat Med. Mar. 2015; 21(3): 248-255.
Marchetti, et al., A Novel Pharmacologic Inhibitor of the NLRP3 Inflammasome Limits Myocardial Injury Following Ischemia-Reperfusion in the Mouse; J Cardiovasc Pharmacol. Apr. 2014; 63(4): 316-322.
Honda, et al., Isoliquiritigenin is a potent inhibitor of NLRP3 inflammasome activation and diet-induced adipose tissue inflammation, J Leukoc Biol. Dec. 2014;96(6):1087-100. Abstract.
Coll, et al., The Cytokine Release Inhibitory Drug CRID3 Targets ASC Oligomerisation in the NLRP3 and AIM2 Inflammasomes, PLoS ONE, Dec. 2011 | vol. 6 | Issue 12, pp. 1-9.
Juliana, et al., Anti-inflammatory Compounds Parthenolide and Bay 11-7082 Are Direct Inhibitors of the Inflammasome, The Journal of Biological Chemistry vol. 285, No. 13, pp. 9792-9802, 2010.
Wannamaker, et al., (S)-1-((S)-{[1-(4-Amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1 and IL-18, The Journal of Pharmacology and Experimental Therapeutics, 2007, vol. 321, No. 2, pp. 509-516.
Lamkanfi, et al., Glyburide inhibits the Cryopyrin/Nalp3 inflammasome, J. Cell Biol. vol. 187 No. 1, pp. 61-70, 2009.
Milligan, et al., Peptide Inhibitors of the ICE Protease Family Arrest Programmed Cell Death of Motoneurons In Vivo and In Vitro, Neuron, vol. 15, Aug. 1995, pp. 385-393.
Kim, et al., Active Caspase-1-Mediated Secretion of Retinoic Acid Inducible Gene-I1, The Journal of Immunology, 2008; 181:7324-7331.
Lee, et al., Cooperation of TLR2 with MyD88, PI3K, and Rac1 in Lipoteichoic Acid-Induced cPLA2/COX-2-Dependent Airway Inflammatory Responses, The American Journal of Pathology vol. 176, Issue 4, Apr. 2010, pp. 1671-1684
Liu, et al., MyD88 expression in the rat dental follicle: implications for osteoclastogenesis and tooth eruption, Oral Sciences & Technology, European Journal of Oral Sciences, vol. 118 Issue 4, Abstract, 2010.
Villa, et al., Selective MyD88-dependent pathway inhibition by the cyanobacterial natural product malyngamide F acetate, European Journal of Pharmacology, vol. 629, Issues 1-3, Mar. 10, 2010, pp. 140-146.

(56) References Cited

OTHER PUBLICATIONS

Kim, et al., Early growth response-1 is involved in foam cell formation and is upregulated by the TLR9-MyD88-ERK1/2 pathway, Biochemical and Biophysical Research Communications, vol. 390, Issue 2, Dec. 11, 2009, Abstract.

Ikebe, et al., Lipopolysaccharide (LPS) increases the invasive ability of pancreatic cancer cells through the TLR4/MyD88 signaling pathway, Journal of Surgical Oncology, Dec. 2009, vol. 100, Issue 8, 15 , abstract.

Yu, et al., Role of MyD88 in TLR agonist-induced functional alterations of human adipose tissue-derived mesenchymal stem cells, Molecular and Cellular Biochemistry, Oct. 2008, vol. 317, Issue 1, abstract.

Ahmad, et al., MyD88, IRAK1 and TRAF6 knockdown in human chondrocytes inhibits interleukin-1-induced matrix metalloproteinase-13 gene expression and promoter activity by impairing MAP kinase activation, Cellular Signalling vol. 19, Issue 12, Dec. 2007, abstract.

Vickers, et al., Modification of MyD88 mRNA Splicing and Inhibition of IL-1 Signaling in Cell Culture and in Mice with a 2-O-Methoxyethyl-Modified Oligonucleotide, The Journal of Immunology, Nov. 5, 2015, pp. 3652-3661.

Nishida, et al., Cloning and expression of a single-chain Fv fragment specific for the human interleukin 18 receptor, Hybridoma. Dec. 1998;17(6):Abstract.

Novick, et al., Interleukin-18 binding protein: a novel modulator of the Th1 cytokine response, Immunity. Jan. 1999;10(1):Abstract.

Reznikov, et al., IL-18 binding protein increases spontaneous and IL-1-induced prostaglandin production via inhibition of IFN-gamma, Proc Natl Acad Sci U S A. Feb. 29, 2000;97(5):2174-9.

Debets, et al., IL-18 Receptors, Their Role in Ligand Binding and Function: Anti-IL-1RAcPL Antibody, a Potent Antagonist of IL-18I, The Journal of Immunology, 2000, pp. 4950-4956.

Im, et al., Suppression of experimental myasthenia gravis, a B cell-mediated autoimmune disease, by blockade of IL-18, FASEB J. Oct. 2001;15(12):2140-8.

Plater-Zyberk, et al., Therapeutic effect of neutralizing endogenous IL-18 activity in the collagen-induced model of arthritis, J Clin Invest., 2001, 108(12), pp. 1825-1832.

Raeburn, et al., Neutralization of IL-18 attenuates lipopolysaccharide-induced myocardial dysfunction, American Journal of Physiology—Heart and Circulatory Physiology Published Aug. 1, 2002 vol. 283 No. 2, H650-H657.

Hamasaki, et al., Human Anti-Human IL-18 Antibody Recognizing the IL-18-Binding Site 3 with IL-18 Signaling Blocking Activity, J. Biochem. (2005) 138, 433-442.

\* cited by examiner

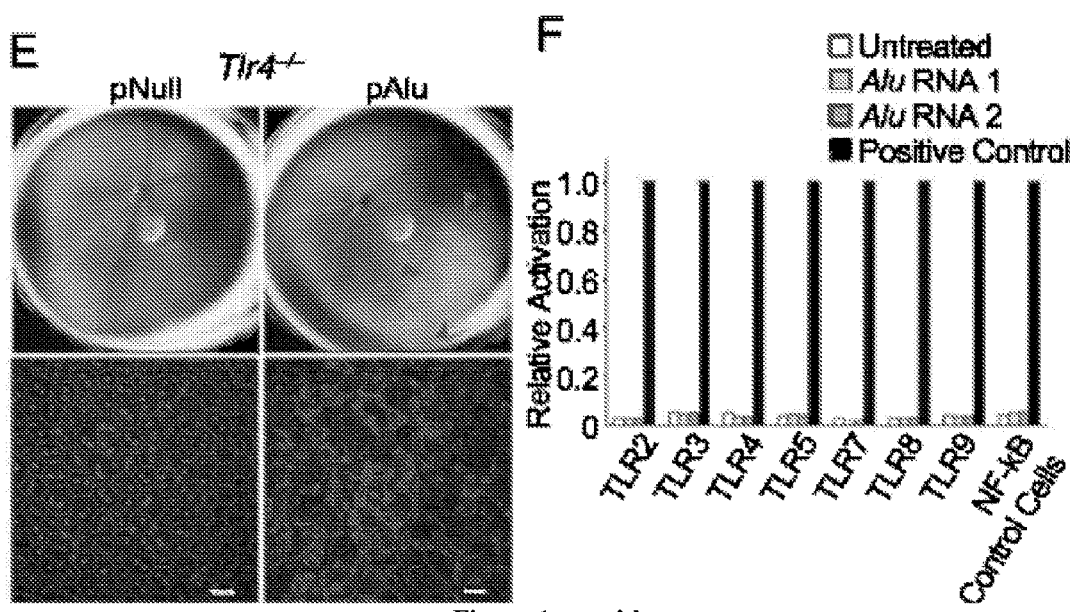
Figure 1, cont'd

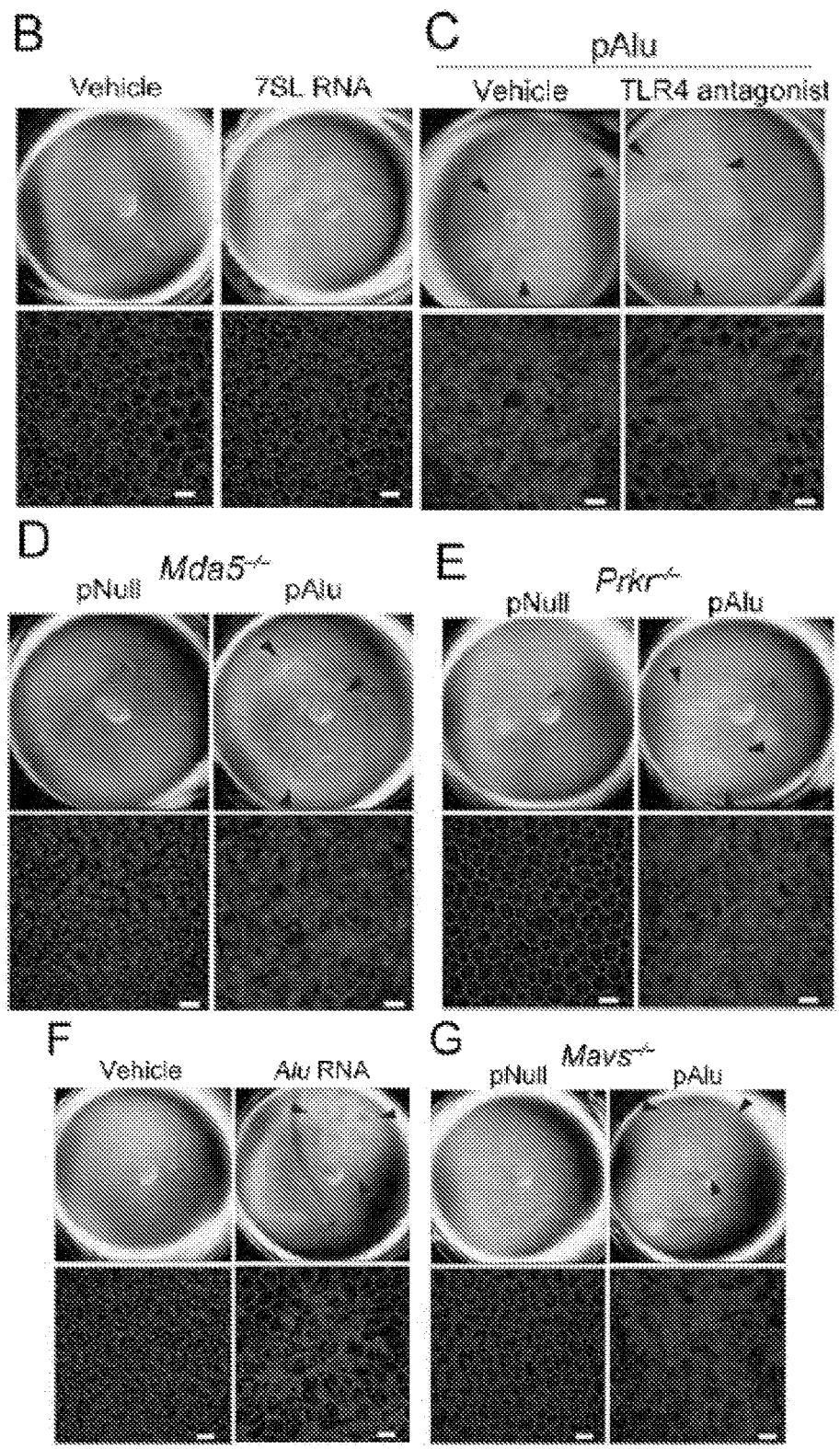
Figure 2, cont'd

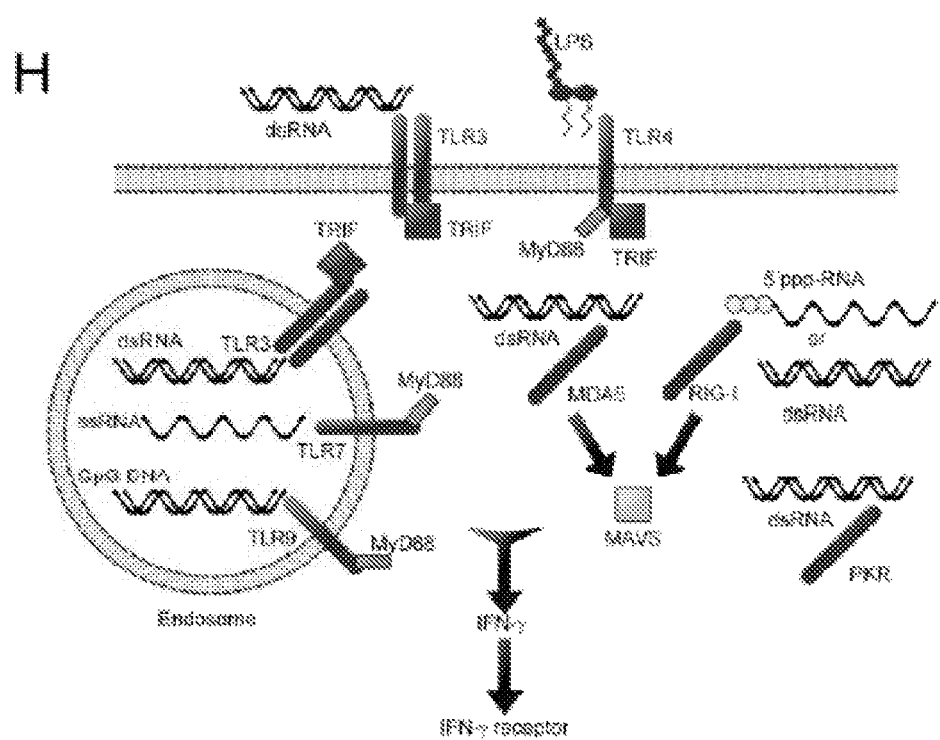
Figure 2, Cont'd

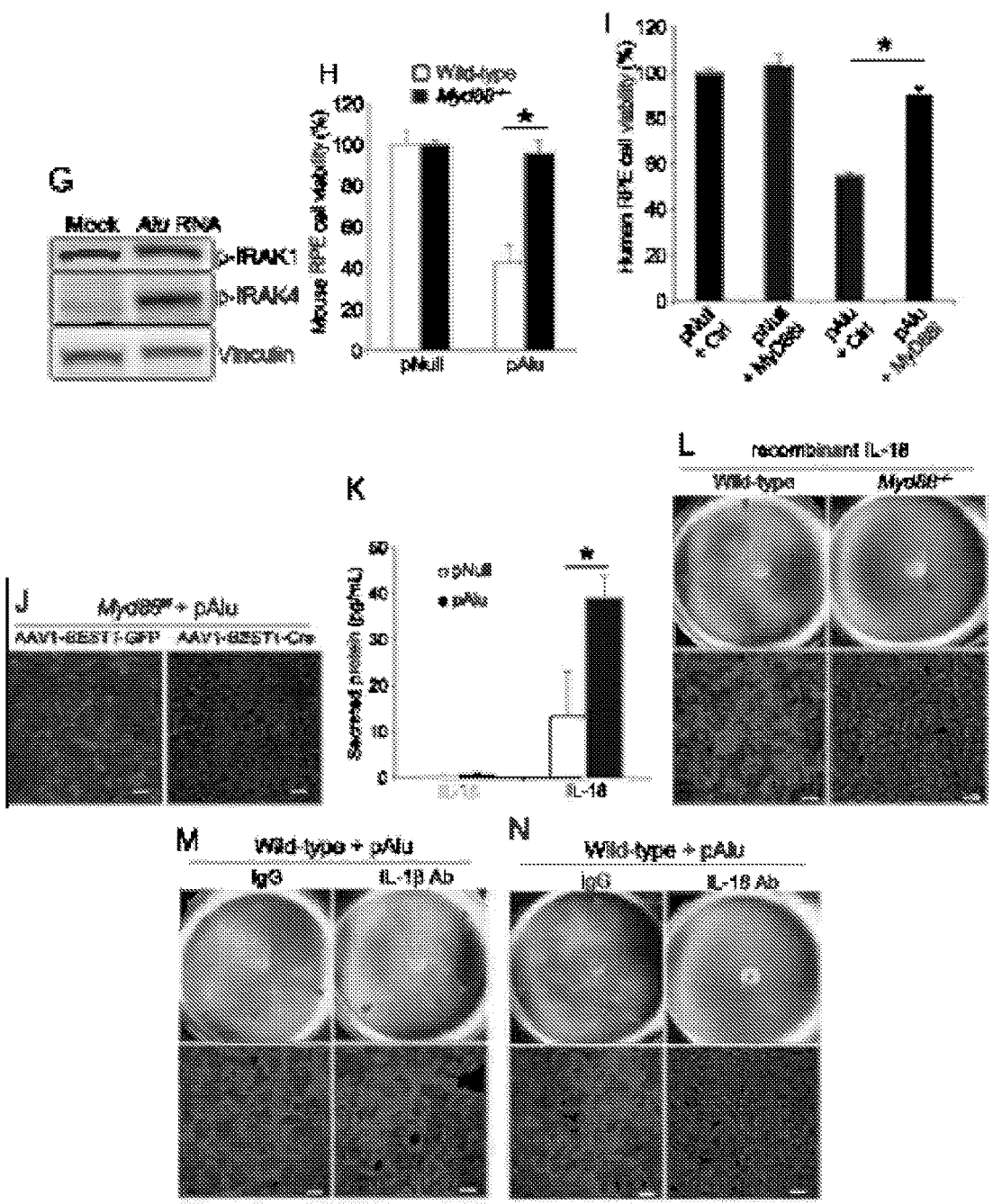
Figure 3, Cont'd

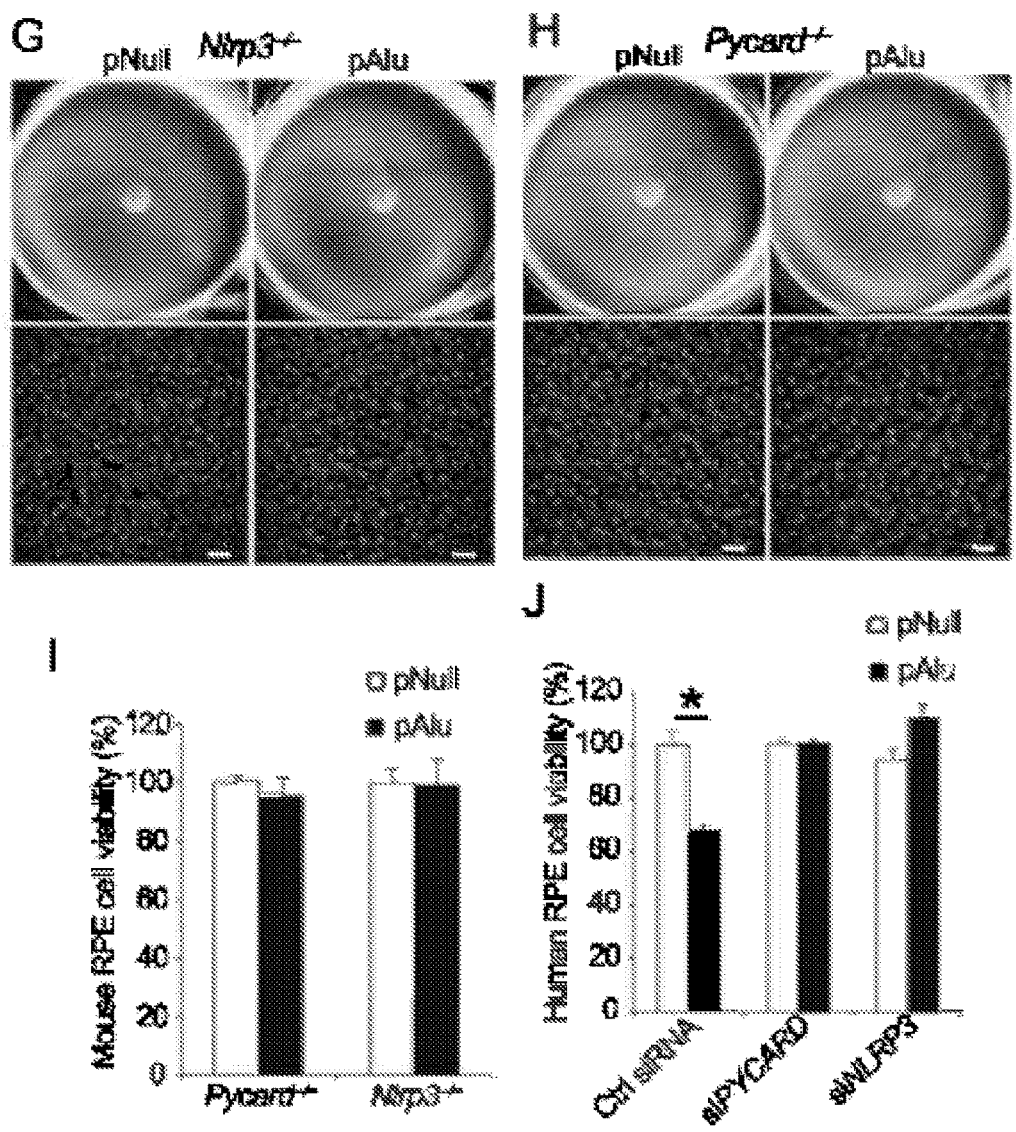
Figure 5, Cont'd

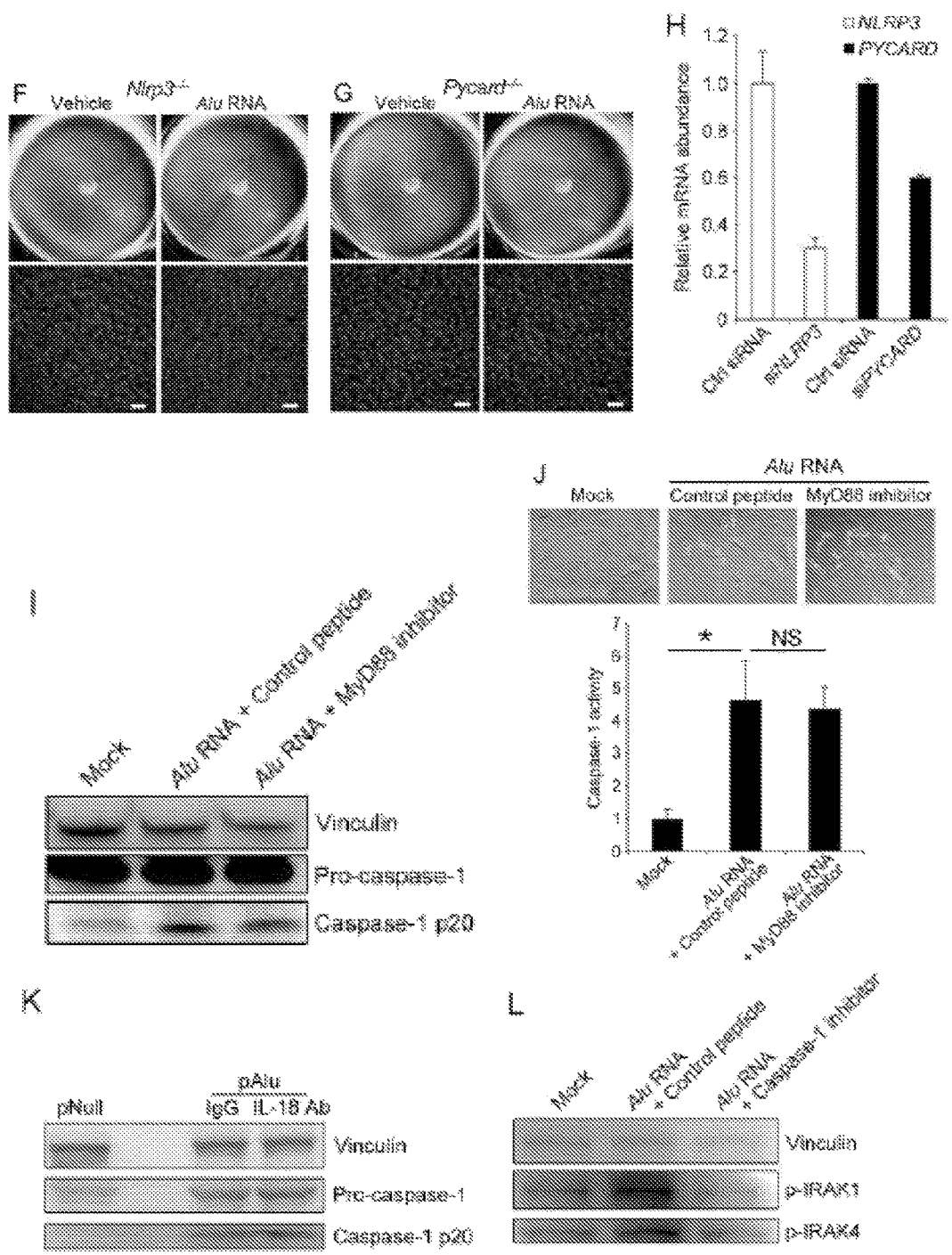
Figure 6, Cont'd

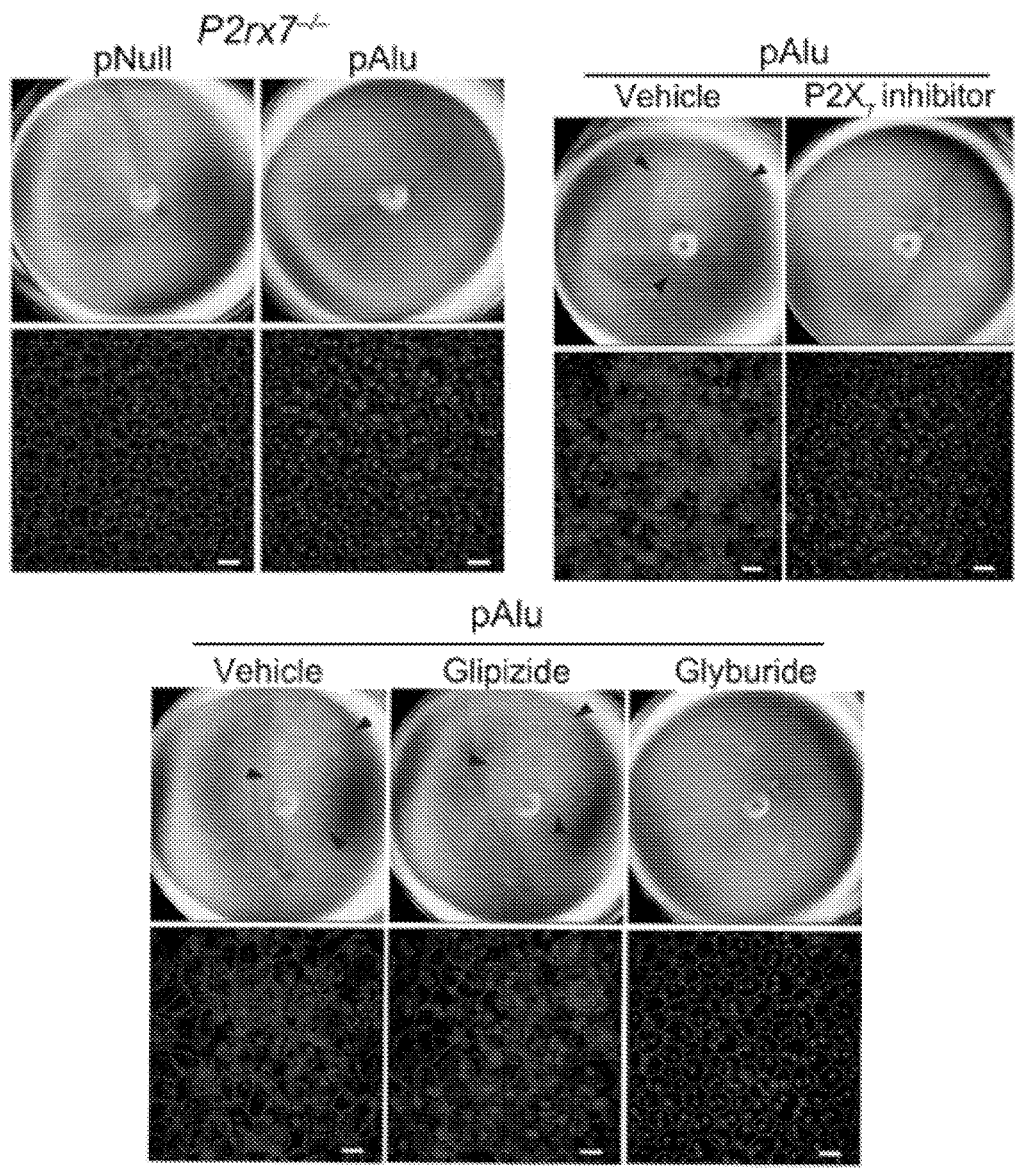
Figure 7, Cont'd

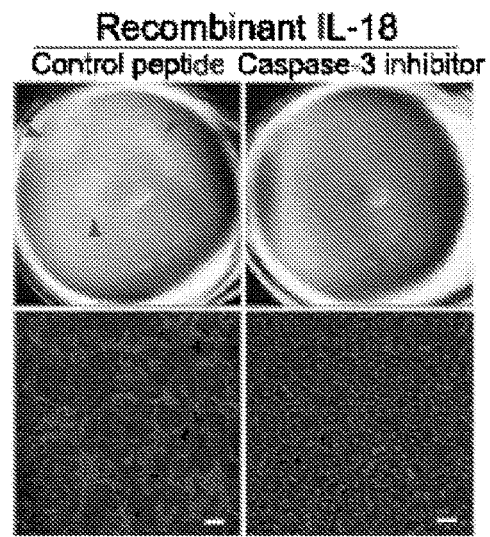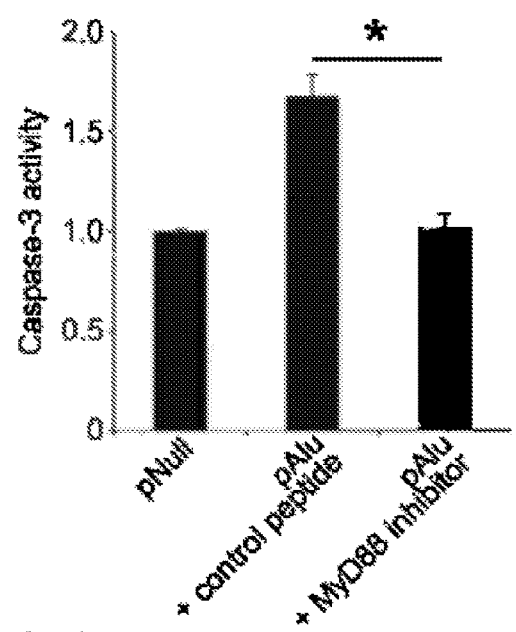
Figure 8, Cont'd

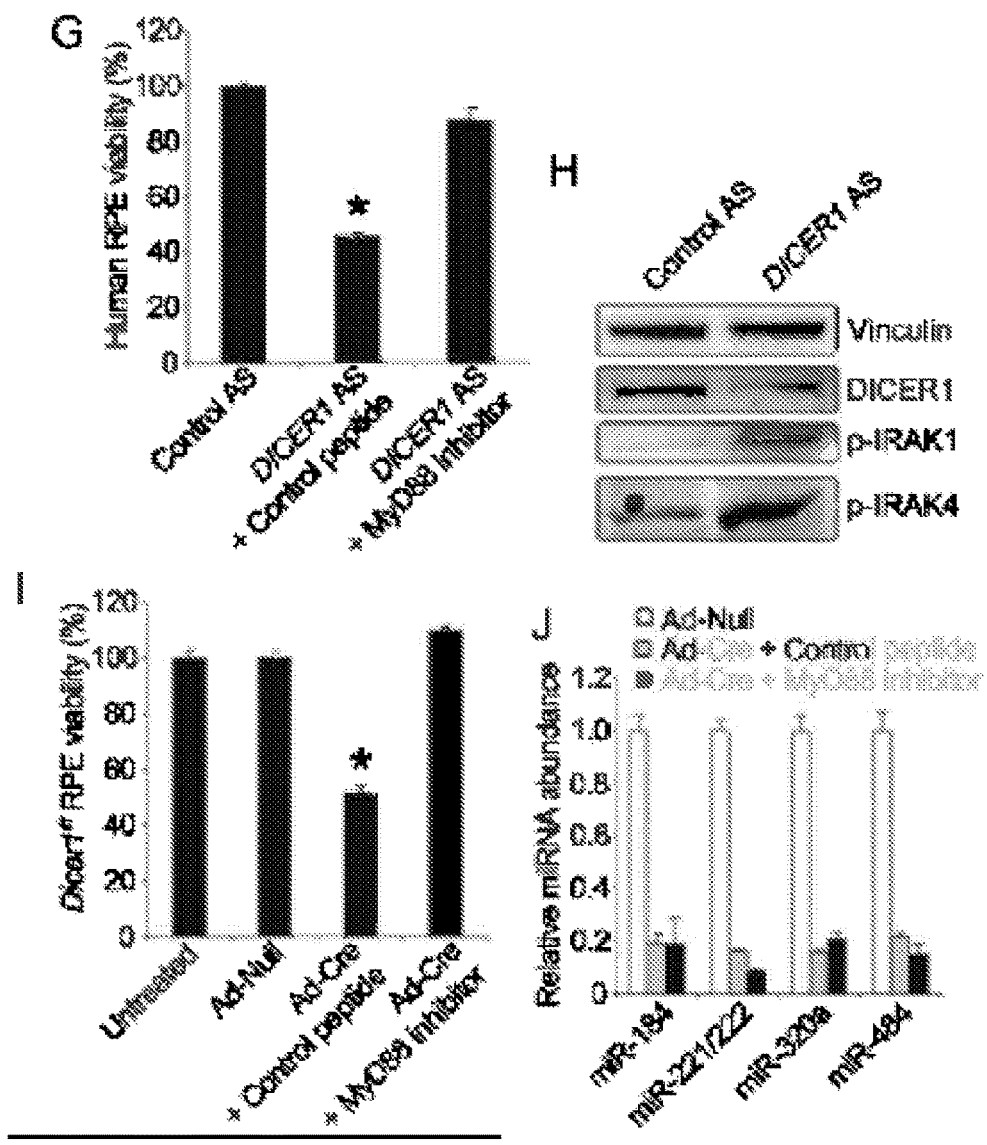
Figure 9, Cont'd

PROTECTION OF CELLS FROM DEGENERATION AND TREATMENT OF GEOGRAPHIC ATROPHY

RELATED APPLICATIONS

This application claims priority from U.S. Provisional Application Ser. No. 61/586,427 filed Jan. 13, 2012, the entire disclosure of which is incorporated herein by this reference.

GOVERNMENT INTEREST

This invention was made with government support under Grant No. EY022238-01 awarded by the National Institutes of Health.

TECHNICAL FIELD

The presently-disclosed subject matter relates to therapeutic uses of inflammasome inhibition, $P2X_7$ inhibition, and inhibition of IRAK1 and/or IRAK4, methods protecting a cell, and screening methods for identifying inhibitors.

INTRODUCTION

Age-related macular degeneration (AMD) is a devastating disease that affects the vision of tens of millions of individuals worldwide (Smith et al., 2001). AMD is characterized by dysfunction and degeneration of the retinal pigmented epithelium (RPE), a highly specialized monolayer of cells that is interposed between the retinal photoreceptors and the choroidal capillaries (Ambati et al., 2003). RPE dysfunction can lead to anatomical and functional disruption of both the photoreceptors and the choroidal vasculature (Blaauwgeers et al., 1999; Lopez et al., 1996; McLeod et al., 2009; Vogt et al., 2011). These tissue architecture disruptions lead to atrophic or neovascular disease phenotypes. Although there are multiple approved therapies for the neovascular form of AMD (Ferrara, 2010), there is no effective treatment for the far more common atrophic form of the disease. GA, the advanced stage of atrophic AMD, is characterized by degeneration and death of the RPE, and is the leading cause of untreatable vision loss.

Recently, it was shown that a dramatic and specific reduction of the RNase DICER1 results in accumulation of Alu RNA transcripts in the RPE of human eyes with GA (Kaneko et al., 2011; International Patent Application No. PCT/US11/38753, Ambati). These repetitive element transcripts, which are non-coding RNAs expressed by the highly abundant Alu retrotransposon (Batzer and Deininger, 2002), induce human RPE cell death and RPE degeneration in mice. DICER1 deficit in GA RPE was not a generic cell death response because DICER1 expression was not dysregulated in a variety of other retinal diseases. Likewise, Alu RNA accumulation did not represent generalized retrotransposon activation due to a stress response in dying cells because several other retrotransposons were not elevated in GA RPE, DICER1 is central in the biogenesis of mature microRNAs (Bernstein et al., 2001). Yet, intriguingly, following DICER1 deficit, the accumulation of Alu RNA transcripts and not the lack of mature microRNAs was the critical determinant of RPE cell viability (Kaneko et al., 2011). Moreover, other RNAs of similar length such as 7SL RNA, transfer RNA, and primary microRNAs do not induce RPE degeneration (Kaneko et al., 2011), ruling out a non-specific toxicity of excess, highly structured RNA. Still, the precise mechanisms of Alu RNA-induced cytotoxicity are unknown.

Although the retina is a tissue exceptional for its immune privilege (Streilein, 2003), its hypersensitive response to exogenous insults mediated by innate immune sensors can result in profound inflammation. The three major classes of innate immune receptors include the toll-like receptors (TLRs), retinoic acid inducible gene I (RIG-I)-like helicases, and nucleotide-binding domain and leucine-rich-repeat-containing (NLR) proteins (Akira et al., 2006). Numerous innate immune receptors have been identified in the RPE (Kumar et al., 2004), and a variety of exogenous substances can induce retinal inflammation (Allensworth et al., 2011; Kleinman et al., 2011). However, it is not known whether this surveillance machinery recognizes or responds to host endogenous RNAs. As described herein, the present inventor explored the concept that innate immune machinery, whose canonical function is the detection of pathogen associated molecular patterns and other moieties from foreign organisms, might also recognize cytotoxic Alu RNA.

As described herein, it was shown that Alu transcripts can hijack innate immunity machinery to induce RPE cell death. Surprisingly, the data set forth herein show that DICER1 deficit or Alu RNA activates the NLRP3 inflammasome in a MyD88-dependent, but TLR-independent manner. Until now, NLRP3 inflammasome activation in vivo has been largely restricted to immune cells, although the findings open the possibility that NLRP3 inflammasome activity may be more widespread than previously thought, as reflected by examples in cell culture studies of keratinocytes (Feldmeyer et al., 2007; Keller et al., 2008). The findings disclosed herein also broaden the scope of DICER1 function beyond microRNA biogenesis, and identify its role as a guardian against the aberrant overexpression of toxic retrotransposon genetic elements that comprise roughly 50% of the human genome (Lander et al., 2001). The findings present a novel self-recognition immune response, whereby endogenous non-coding RNA-induced NLRP3 inflammasome activation results from DICER1 deficiency in a non-immune cell. Also proposed herein are unique targets for protecting RPE cells against cell death, including $P2X_7$ activation and IRAK-1/4.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method of protecting a cell, which involves inhibiting one or more of P2X7 activation associated with or in the cell, inhibiting IRAK1 associated with or in the cell; or inhibiting IRAK4 associated with or in the cell.

In some embodiments, the cell is an RPE cell, a retinal photoreceptor, or a choroidal cell. In some embodiments, the cell is in a subject. In some embodiments, the cell is an RPE cell, and the method also involves identifying a subject for which protection of the RPE cell is desired. In some embodiments, the cell is an RPE cell is of a subject having age-related macular degeneration. In some embodiments, contacting the cell with an inhibitor comprises administering the inhibitor to a subject.

In some embodiments of the method, the inhibiting of P2X7 activation includes contacting the cell with a P2X7 activation inhibitor, e.g., P2X7 receptor antagonist A438079.

In some embodiments of the method, inhibiting IRAK1 and/or IRAK 4 includes contacting the cell with an IRAK1 and/or IRAK4 inhibitor (e.g., N-(2-Morpholinylethyl)-2-(3-nitrobenzoylamido)-benzimidazole).

In some embodiments the method can also include inhibiting MyD88 associated with or in the cell; inhibiting IL-18 associated with or in the cell; inhibiting an inflammasome associated with or in the cell; increasing levels of a DICER polypeptide associated with or in the cell; and/or inhibiting AluRNA associated with or in the cell.

The presently-disclose d subject matter also includes a method of treating macular degeneration, which involves identifying a subject in need of treatment for macular degeneration; and inhibiting P2X7 activation associated with or in a cell of the subject; inhibiting IRAK1 associated with or in a cell of the subject; inhibiting IRAK4 associated with or in a cell of the subject; inhibiting MyD88 associated with or in the cell; inhibiting IL-18 associated with or in the cell; inhibiting an inflammasome associated with or in the cell; increasing levels of a DICER polypeptide associated with or in the cell; and/or inhibiting AluRNA associated with or in the cell.

In some embodiments of the method, the inhibiting MyD88 associated with or in the cell includes contacting the cell with a MyD88 inhibitor. In some embodiments of the method, the inhibiting of P2X7 activation includes contacting the cell with a P2X7 activation inhibitor (e.g., P2X7 receptor antagonist A438079). In some embodiments of the method, the inhibiting IRAK1 and/or IRAK 4 includes contacting the cell with an IRAK1 and/or IRAK4 inhibitor (e.g., N-(2-Morpholinylethyl)-2-(3-nitrobenzoylamido)-benzimidazole).

The presently-disclosed subject matter further includes kits useful for practicing methods as disclosed herein. In some embodiments, the kit includes a P2X7 activation inhibitor, packaged together with an IRAK1 and/or IRAK4 inhibitor. In some embodiments, the kit also includes a MyD88 inhibitor, an IL-18 inhibitor, an inflammasome inhibitor, a DICER polypeptide, and an AluRNA inhibitor.

The presently-disclosed subject matter further includes a method of identifying an IRAK1 and/or IRAK4 inhibitor, which involves providing a cultured cell wherein phosphorylated IRAK1 and/or IRAK4 is upregulated; contacting the cell with a candidate compound; and determining whether the candidate compound results in a change in the IRAK1 and/or IRAK4. In some embodiments, the IRAK1 and/or IRAK4 is upregulated by stimulating the cell with a MyD88 activator. In some embodiments, the method further includes measuring phosphorylation of IRAK1 and/or IRAK4 by Western Blotting. In some embodiments, the change in the IRAK1 and/or IRAK4 is monitored by measuring cell viability, or measuring the expression of a gene known to be induced by IRAK1 and/or IRAK 4 signaling.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
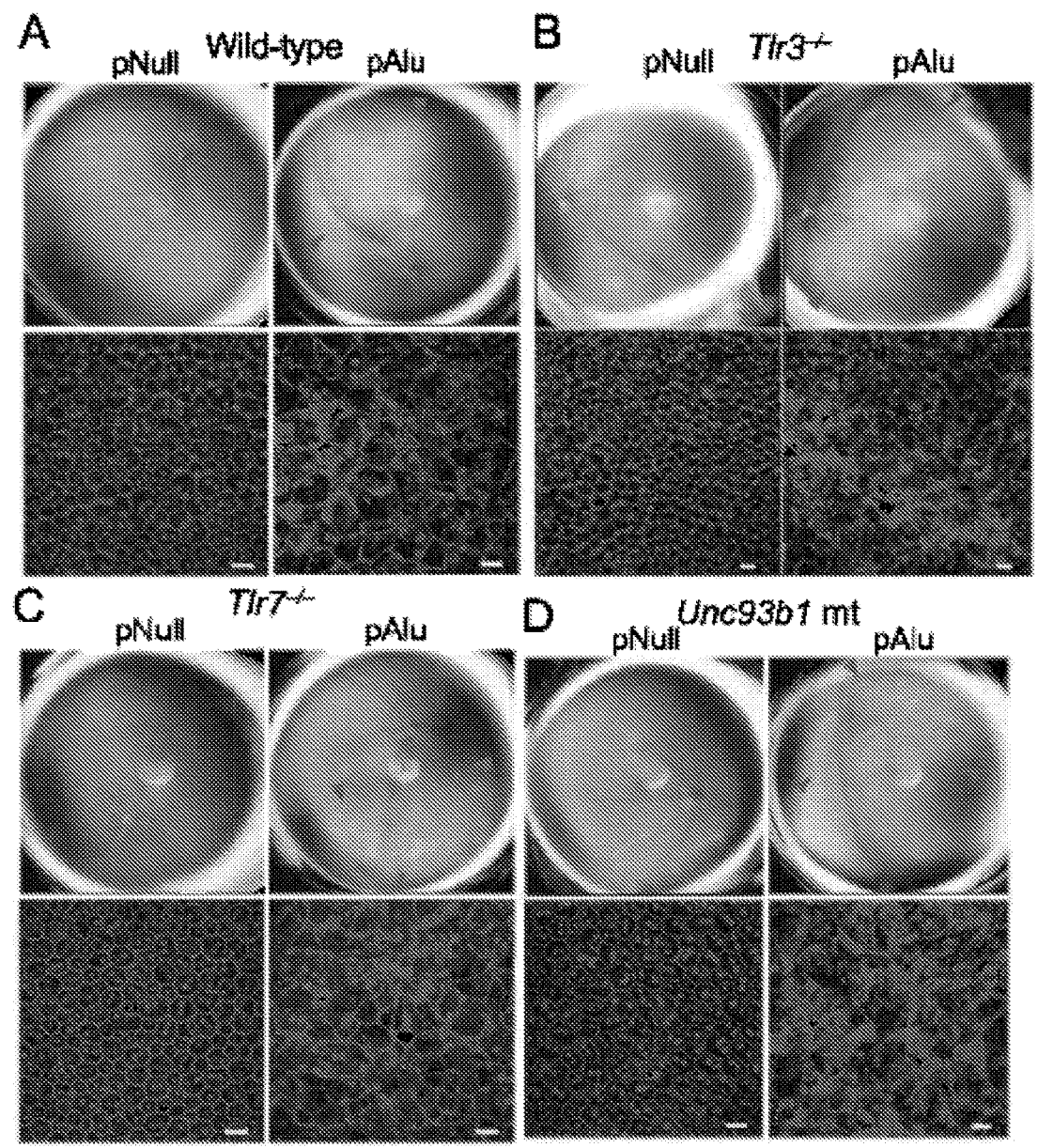
FIG. 1. Alu RNA does not activate or function via toll-like receptors (TLRs). (A-E) Subretinal injection of a plasmid coding for Alu RNA (pAlu), but not pNull, induces retinal pigmented epithelium (RPE) degeneration in wild-type mice (A) and in mice deficient in Tlr3 (B) or Tlr7 (C), mice with a mutation (mt) in Unc93b1 (D), which are functionally deficient in TLRs-3,7,9, or deficient in Tlr4 (E). Representative images shown. n=8-12. Fundus photographs, top row; Flat mounts stained for zonula occludens-1 (ZO-1; red), bottom row. Degeneration outlined by blue arrowheads. Scale bars, 20 μm. (F) Stimulation of HEK293 cell lines expressing various TLRs with either of two different Alu RNA sequences does not elicit NF-κB activation as assessed by measuring a secreted alkaline phosphatase reporter under the control of a NF-κB-inducible promoter. Positive (+) controls using TLR-specific ligands activated NF-κB. n=3.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods for inhibiting P2X$_7$ activation and therapeutic and protective uses thereof. Also provided are method for inhibiting IRAK1 and therapeutic and protective uses thereof. Also provided are methods for inhibiting IRAK4 and therapeutic and protective uses thereof. Also provided are methods for identifying inhibitors.

In some embodiments, the presently-disclosed subject matter includes a method of protecting a cell, which involves inhibiting one or more of P2X7 activation associated with or in the cell, inhibiting IRAK1 associated with or in the cell; or inhibiting IRAK4 associated with or in the cell. The cell being protected can be, for example, an RPE cell, a retinal photoreceptor, or a choroidal cell. In some embodiments, the cell is in a subject. In some embodiments, the cell is an RPE cell. In some embodiments, the method includes identifying a subject for which protection of an RPE cell is desired. In some embodiments of the method, the cell is an RPE cell of a subject having age-related macular degeneration.

As will be recognized by one of ordinary skill in the art, the term "protecting" or "protection" when used with reference to a cell or group of cells does not refer to an ability to complete eliminate all instances of cell death. Rather, the skilled artisan will understand that the term "protecting" refers to a reduction in cytotoxicity for a cell or group of cells, or to a reduction in the likelihood of cell death for a cell or group of cells, e.g., Alu-RNA-induced cytotoxicity or cell death. Such reduction can be a reduction by at least about 50%, at least about 75%, at least about 90%, or at least about 95% of the cytotoxicity/cell death of a cellular population. Such reduction can be determined relative to a control, e.g., in the absence of $P2X_7$ activation inhibitor, IRAK-1 inhibitor, and/or IRAK-4 inhibitor.

An inhibitor as described herein can be a polypeptide inhibitor (including oligonucleotide inhibitor), a small molecule inhibitor, or an siRNA inhibitor. It is noted that, the terms "inhibit", "inhibitor", or "inhibiting" are not meant to require complete inhibition, but refers to a reduction in signaling. Such reduction can be a reduction by at least about 50%, at least about 75%, at least about 90%, or at least about 95% of the signaling in the absence of the inhibitory effect, e.g., in the absence of a compound that is an inhibitor of the signaling.

In some embodiments of the presently-disclosed subject matter, a method of protecting a cell can include inhibiting of $P2X_7$ activation associated with or in the cell of the subject. In some embodiments, the method further includes identifying a subject in need of treatment for a condition of interest. In some embodiments, inhibiting $P2X_7$ activation includes contacting the cell with a $P2X_7$ activation inhibitor. In some embodiments, contacting the cell with the inhibitor comprises administering the inhibitor to a subject. Such inhibitors can be administered, for example, by topical, intravitreous, subretinal, peribulbar, suprachoroidal, intracapsular, intravenous, intramuscular, or subcutaneous administration, or by inhalational of the inhibitor.

Examples of appropriate $P2X_7$ activation inhibitors include, but are not limited to a $P2X_7$ receptor antagonist (e.g., A438079), an inhibitor of the activation of the $P2X_7$ receptor, or an inhibitor of the expression of $P2X_7$ (including, for example, inhibition of transcription of the P2RX7 gene, and inhibition of translation of a product of the P2RX7 gene, including by use of RNA interference technologies). Examples of inhibitors include, polypeptide inhibitors (which include oligonucleotide inhibitors), small molecule inhibitors, and siRNA inhibitors.

In some embodiments of the presently-disclosed subject matter, a method of protecting a cell can include inhibiting IRAK1 and/or IRAK 4 associated with or in the cell of the subject. In some embodiments, the method further includes identifying a subject in need of treatment for a condition of interest. In some embodiments, inhibiting IRAK1 and/or IRAK 4 includes contacting the cell with a IRAK1 and/or IRAK 4 inhibitor. In some embodiments, contacting the cell with the inhibitor comprises administering the inhibitor to a subject. Such inhibitors can be administered, for example, by topical, intravitreous, subretinal, peribulbar, suprachoroidal, intracapsular, intravenous, intramuscular, or subcutaneous administration, or by inhalational of the inhibitor. Examples of appropriate IRAK1 and/or IRAK 4 inhibitors include, an antagonist, such as a small molecule antagonist, or an inhibitor of the expression of IRAK1, and/or IRAK4 (including, for example, inhibition of transcription and inhibition of translation, including by use of RNA interference technologies). Examples of inhibitors include, polypeptide inhibitors (which include oligonucleotide inhibitors), small molecule inhibitors, and siRNA inhibitors. Specific examples of inhibitors that can be used in accordance with the presently-disclosed subject matter include but are not limited to N-(2-Morpholinylethyl)-2-(3-nitrobenzoylamido)-benzimidazole, and other examples are described, for example, in Buckley, G. M, et al., (2008) "IRAK-4 inhibitors. Part III: A series of imidazo[1,2-a]pyridines" *Bioorganic & Medicinal Chemistry Letters,* 18:656-3660, and other known IRAK inhibitors, including those being developed by Merck (e.g., eshop.emdchemicals.com) and Ligand Pharmaceuticals (e.g., www.ligand.com/irak4-inhibitor).

The methods as described herein can further include inhibiting MyD88 associated with or in a cell of the subject; inhibiting IL-18 associated with or in a cell of the subject; inhibiting an inflammasome associated with or in a cell of the subject; increasing levels of a DICER polypeptide associated with or in a cell of the subject; and/or inhibiting AluRNA associated with or in a cell of the subject. Relevant information and details regarding such additional steps of embodiments of the presently-disclosed subject matter can be found, for example, in U.S. Provisional Patent Application No. 61/543,038; U.S. Provisional Patent Application No. 61/508,867; and International Patent Application No. PCT/US11/38753, each of which is incorporated herein by reference.

In some embodiments, the method of protecting a cell as described herein can be useful for the treatment of a condition of interest, for example, a condition selected from: Geographic atrophy; Macular degeneration; Alzheimer disease; Cryopyrinopathies; Inflammatory Bowel Disease; Keratitis; Gout; Acne vulgaris; Crohn's disease; Ulcerative colitis; Irritable bowel syndrome; Type I diabetes; Type 2 diabetes; Insulin resistance; Obesity; Hemolytic-Uremic Syndrome; Polyoma virus infection; Immune complex renal disease; Acute tubular injury; Lupus nephritis; Familial cold autoinflammatory syndrome; Muckle-Wells syndrome and neonatal onset multisystem inflammatory disease; Chronic infantile neurologic cutaneous and articular autoinflammatory diseases, Renal ischemia-perfusion injury; Glomerulonephritis; Cryoglobulinemia; Systemic vasculitides; IgA nephropathy Atherosclerosis; HIV/AIDS; Malaria; Helminth parasites; Sepsis and septic shock; Allergic asthma; Hay fever; Chronic obstructive pulmonary disease; Drug-induced lung inflammation; Contact dermatitis; Leprosy; *Burkholderia cenocepacia* infection; Respiratory syncitial virus infection; Psoriasis; Systemic lupus erythematosus; Scleroderma; Reactive arthritis; Cystic fibrosis, Syphilis, Sjögren's syndrome; Rheumatoid arthritis; Inflammatory joint disease; Non-alcoholic fatty liver disease; Cardiac surgery (peri-/post-operative inflammation); Acute and chronic organ transplant rejection; Acute and chronic bone marrow transplant rejection; and Tumor angiogenesis. In some embodiments, the condition of interest is geographic atrophy and the cell is an RPE cell. In this regard, a subject having age-related macular degeneration can be treated using methods and compositions as disclosed herein. It is noted that macular degeneration refers to both a dry form of macular degeneration (e.g., geographic atrophy/retinal degeneration), as well as a wet form of macular degeneration (e.g., angiogenesis/blood vessel growth). In this regard, inhibitors as disclosed herein can be useful for treating all forms of macular degeneration. By way of specific example, a MyD88 inhibitor can be used to treat various forms of macular degeneration, and is specifically contemplated for inhibition of choroidal neovascularization.

As used herein, the terms treatment or treating relate to any treatment of a condition of interest, including but not limited to prophylactic treatment and therapeutic treatment.

As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

As used herein, the term "subject" refers to a target of treatment. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter.

The terms "polypeptide", "protein", and "peptide", which are used interchangeably herein, refer to a polymer of the 20 protein amino acids, or amino acid analogs, regardless of its size. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, from internal portions of the reference polypeptide, or a combination thereof. A fragment can also be a "functional fragment," in which case the fragment retains some or all of the activity of the reference polypeptide as described herein.

The terms "modified amino acid", "modified polypeptide", and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. The term functional variant includes a functional variant of a functional fragment of a reference polypeptide.

The presently-disclosed subject matter further includes a kit, useful for practicing the methods as disclosed herein. In some embodiments, the kit can include a P2X7 activation inhibitor, packaged together with an IRAK1 and/or IRAK4 inhibitor. In some embodiments, the kit can also include an IL-18 inhibitor, an inflammasome inhibitor, a DICER polypeptide, and an AluRNA inhibitor.

The presently-disclosed subject matter also includes a method for identifying an IRAK1 and/or IRAK 4 inhibitor, including providing a cultured cell wherein phosphorylated IRAK1 and/or IRAK4 is upregulated; contacting the cell with a candidate compound; and determining whether the candidate compound results in a change in the IRAK1 and/or IRAK4. The IRAK1 and/or IRAK4 can be upregulated in the cell, for example, by stimulating the cells with a MyD88 activator (e.g., Alu-RNA, LPS) and measuring phosphorylation (activation) of IRAK1 and/or IRAK4 by Western blotting. The change in the IRAK1 and/or IRAK4 can monitored, for example, by measuring cell viability, or measuring the expression of a gene known to be induced by IRAK 1 and/or IRAK 4 signaling.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Subretinal Injection and Imaging.

Subretinal injections (1 μL) in mice were performed using a Pico-Injector (PLI-100, Harvard Apparatus). In vivo transfection of plasmids was achieved using 10% Neuroporter (Genlantis). Fundus imaging was performed on a TRC-50 IX camera (Topcon) linked to a digital imaging system (Sony). Immunolabeling of RPE flat mounts was performed using antibodies against human zonula occludens-1 (Invitrogen).

Cell Viability.

Cell viability measurements were performed using the CellTiter 96 AQueous One Solution Cell Proliferation Assay (Promega) in according to the manufacturer's instructions.

mRNA Abundance.

Transcript abundance was quantified by real-time RT-PCR using an Applied Biosystems 7900 HT Fast Real-Time PCR system using the $2^{-\Delta\Delta Ct}$ method.

Protein Abundance and Activity.

Protein abundance was assessed by Western blot analysis using primary antibodies recognizing Caspase-1 (1:500; Invitrogen), pIRAK1 (1:500; Thermo Scientific), pIRAK4 (1:500, Abbomax, Inc), PYCARD (1:200, Santa Cruz Biotechnology), NLRP3 (1:500, Enzo Life Sciences) and Vinculin (1:1,000; Sigma-Aldrich). Caspase-1 activity was visualized using Caspalux1 E1D2 (OncoImmunin) reagent according to the manufacturer's instructions.

Mice.

All animal experiments were approved by institutional review committees and in accordance with the Association for Research in Vision and Ophthalmology Statement for the Use of Animals in Ophthalmic and Visual Research. Wild-type C57BL/6J, $Tlr3^{-/-}$, $Tlr4^{-/-}$ (C57BL/10ScNJ), $Trif^{-/-}$ ($Ticam1^{Lps2}$), $Ifng^{-/-}$, $Ifngr1^{-/-}$, $Il1r1^{-/-}$, $Il18r1^{-/-}$, $P2rx7^{-/-}$, $Myd88^{f/f}$, and $Dicer1^{f/f}$ mice were purchased from The Jackson Laboratory. $Casp1^{-/-}$, $Nlrp3^{-/-}$, and $Pycard^{-/-}$ mice have been previously described (Kanneganti et al., 2006). Unc93b1 mutant mice were generously provided by B. A. Beutler via K. Fitzgerald. $Myd88^{-/-}$ and $Tlr7^{-/-}$ mice were generously provided by S. Akira via T. Hawn and D. T. Golenbock. $Mda5^{-/-}$ mice were generously provided by M. Colonna. $Prkr^{-/-}$ mice were generously provided by B. R. Williams and R. L. Silverman. $Mavs^{-/-}$ mice were generously provided by Z. Chen via K. Fitzgerald. For all procedures, anesthesia was achieved by intraperitoneal injection of 100 mg/kg ketamine hydrochloride (Ft. Dodge Animal Health) and 10 mg/kg xylazine (Phoenix Scientific), and pupils were dilated with topical 1% tropicamide (Alcon Laboratories).

Fundus Photography.

Retinal photographs of dilated mouse eyes were taken with a TRC-50 IX camera (Topcon) linked to a digital imaging system (Sony).

Human Tissue.

Donor eyes or ocular tissues from patients with geographic atrophy due to AMD or age-matched patients without AMD were obtained from various eye banks. These diagnoses were confirmed by dilated ophthalmic examination prior to acquisition of the tissues or eyes or upon examination of the eye globes post mortem. The study followed the guidelines of the Declaration of Helsinki. Institutional review boards granted approval for allocation and histological analysis of specimens.

Immunolabeling.

Human eyes fixed in 2-4% paraformaldehyde were prepared as eyecups, cryoprotected in 30% sucrose, embedded in optimal cutting temperature compound (Tissue-Tek OCT; Sakura Finetek), and cryosectioned into 10 μm sections. Depigmentation was achieved using 0.25% potassium permanganate and 0.1% oxalic acid. Immunohistochemical staining was performed with the rabbit antibody against NLRP3 (1:100, Sigma Aldrich) or rabbit antibody against Caspase-1 (prediluted, AbCam). Isotype IgG was substituted for the primary antibody to assess the specificity of the staining. Bound antibody was detected with biotin-conjugated secondary antibodies, followed by incubation with ABC reagent and visualized by Vector Blue (Vector Laboratories). Levamisole (Vector Laboratories) was used to block endogenous alkaline phosphatase activity. Slides were washed in PBS, counterstained with neutral red (Fisher Scientific), rinsed with deionized water, air dried, and then mounted in Vectamount (Vector Laboratories). Fluorescent labeling of human tissue was performed with the rabbit antibody against PYCARD (1:50, Clone N-15, Santa Cruz Biotechnology). Immunolabeling was visualized by fluorescently conjugated anti-rabbit secondary antibody (Invitrogen). Tissue autofluorescence was quenched by incubating the sections in 0.3% Sudan black (Fisher Scientific). Sections were mounted in Vectashield with DAPI (Vector Laboratories). Mouse RPE/choroid flat mounts were fixed with 4% paraformaldehyde or 100% methanol, stained with rabbit antibodies against human zonula occludens-1 (1:100, Invitrogen) and visualized with Alexa594 (Invitrogen). All images were obtained using the Leica SP-5 or Zeiss Axio Observer Z1 microscopes.

Subretinal Injection.

Subretinal injections (1 μL) in mice were performed using a Pico-Injector (PLI-100, Harvard Apparatus). In vivo transfection of plasmids coding for two different Alu sequences (pAlu) or empty control vector (pNull) (Bennett et al., 2008; Kaneko et al., 2011; Shaikh et al., 1997) was achieved using 10% Neuroporter (Genlantis). AAV1-BEST1-Cre (Alexander and Hauswirth, 2008) or AAV1-BEST1-GFP were injected at $1.0 \times 10^{11}$ pfu/mL and in vitro transcribed Alu RNA was injected at 0.3 mg/mL.

Drug Treatments.

siRNAs formulated in siRNA buffer (20 mM KCL, 0.2 mM MgCl2 in HEPES buffer at pH 7.5; Dharmacon) or phosphate buffered saline (PBS; Sigma-Aldrich); the TLR4 antagonist Ultra Pure *Rhodobacter sphaeroides* LPS (LPS-RS, InvivoGen), a peptide inhibitor of MyD88 homodimerization IMG-2005 (IMGENEX), control inhibitor (IMGENEX), recombinant IL-18 (Medical & Biological Laboratories), neutralizing rat antibodies against mouse IL-1β (IMGENEX), neutralizing rat antibodies against mouse IL-18 (Medical & Biological Laboratories), isotype control IgGs (R&D Systems or eBioscience as appropriate), Caspase-1 inhibitor Z-WEHD-FMK (R&D Systems), Caspase-3 inhibitor Z-DEVD-FMK (R&D Systems), Caspase control inhibitor Z-FA-FMK (R&D Systems), (2R,4R)-APDC (Enzo Life Sciences), Glipizide (Sigma-Aldrich), Glyburide (Sigma-Aldrich), and $P2X_7$ receptor antagonist A438079 (Tocris Bioscience) were dissolved in phosphate buffered saline (PBS; Sigma-Aldrich) or dimethyl sulfoxide (DMSO; Sigma-Aldrich), and injected into the vitreous humor in a total volume of 1 μL with a 33-gauge Exmire microsyringe (Ito Corporation). To assess the effect of MyD88 blockade on pAlu-induced RPE degeneration, 1 μL of cholesterol (chol) conjugated MyD88 siRNA (17+2 nt; 2 μg/μL) was intravitreously injected 1 day after pAlu injection. As a control, Luc siRNA-chol (17+2 nt) was used with identical dosages.

Bone Marrow Chimeras.

Bone marrow transplantation was used to create $Myd88^{-/-}$ chimera mice wherein the genetic deficiency of Myd88 was confined to either circulating cells ($Myd88^{-/-}$ →WT) or nonhematopoietic tissue (WT→$Myd88^{-/-}$). Briefly, bone marrows were collected from femur and tibia of congenic WT or $Myd88^{-/-}$ donor mice by flushing with RPMI1640. After two washing steps, cells were resuspended in RPMI1640. $1\times10^7$ cells in 150 μL of RPMI1640 were injected into the tail vein of irradiated donor mice. Two chimera groups were generated: WT→Myd88$^{-/-}$ (WT cells into Myd88$^{-/-}$ mice) and Myd88$^{-/-}$ →WT (Myd88$^{-/-}$ cells into WT mice). 2 months after bone marrow transfer, mice were injected subretinally with Alu RNA, vehicle, pAlu, or pNull, and monitored for RPE degeneration 7 days later.

Real-Time PCR.

Total RNA was extracted from tissues or cells using Trizol reagent (Invitrogen) according to manufacturer's recommendations, DNase treated and reverse transcribed (QuantiTect, Qiagen). The RT products (cDNA) were amplified by real-time quantitative PCR (Applied Biosystems 7900 HT Fast Real-Time PCR system) with Power SYBR green Master Mix. Oligonucleotide primers specific for human IL1B, human NLRP3, human 18S rRNA, mouse Myd88, mouse Nlrp3, mouse Il18, and mouse 18S rRNA were used. The QPCR cycling conditions were 50° C. for 2 min, 95° C. for 10 min followed by 40 cycles of a two-step amplification program (95° C. for 15 s and 58° C. for 1 min). At the end of the amplification, melting curve analysis was applied using the dissociation protocol from the Sequence Detection system to exclude contamination with unspecific PCR products. The PCR products were also confirmed by agarose gel and showed only one specific band of the predicted size. For negative controls, no RT products were used as templates in the QPCR and verified by the absence of gel-detected bands. Relative expressions of target genes were determined by the $2^{-\Delta\Delta ct}$ method.

miRNA Quantification.

Total RNA containing miRNAs was polyadenylated and reverse transcribed using universal primer using the All-In-One miRNA q-RT-PCR Detection Kit (GeneCopoeia) according to the manufacturer's specifications using a universal reverse primer in combination with forward primers for: mouse miR-184; mouse miR-221/222; mouse miR-320a; and mouse miR-484. miRNA levels were normalized to levels of U6 snRNA using the $2^{-\Delta\Delta ct}$ method. Detection was achieved by SYBR green qPCR with the following conditions: 95° C. for 10 min followed by 40 cycles of 95° C. for 10 s, 60° C. for 20 s and 72° C. for 20 s. Amplicon specificity was assessed by melt curve analysis and unique bands by agarose gel electrophoresis.

Western Blotting.

Tissues or cells were homogenized in lysis buffer (10 mM Tris base, pH 7.4, 150 mM NaCl, 1 mM EDTA, 1 mM EGTA, 1% Triton X-100, 0.5% NP-40, protease and phosphatase inhibitor cocktail (Roche)). Protein concentrations were determined using a Bradford assay kit (Bio-Rad) with bovine serum albumin as a standard. Proteins (40-100 μg) were run on NuPAGE Bis-Tris gels (Invitrogen) and transferred to Immun-Blot PVDF membranes (Bio-Rad). Cells were scraped in hot Laemmli buffer (62.5 mM Tris base, pH 6.8, 2% SDS, 5% 2-Mercaptoethanol, 10% Glycerol, 0.01% Bromophenol Blue). Samples were boiled and run on 4-20% NuPAGE Tris-Glycine gels (Invitrogen). The transferred membranes were blocked for 1 h at RT and incubated with antibodies against human Caspase-1 (1:500; Invitrogen), mouse Caspase1 (1:500; MBL), NLRP3 (1:1000; Enzo Life Sciences), PYCARD (1:1000, RayBiotech), phospho-IRAK1 (S376) (1:500, Thermo Scientific), phospho-IRAK4 (T345) (1:500, AbboMax), DICER1 (1:2,000; Bethyl), MyD88 (1:1,000; Cell Signaling), and mouse IL-18 (1:200; MBL) at 4° C. overnight. Protein loading was assessed by immunoblotting using an anti-Vinculin antibody (1:1,000; Sigma-Aldrich). The secondary antibodies were used (1:5, 000) for 1 h at RT. The signal was visualized by enhanced chemiluminescence (ECL plus) and captured by VisionWorksLS Image Acquisition and Analysis software (Version 6.7.2, UVP, LLC).

Cell Culture.

All cell cultures were maintained at 37° C. and 5% $CO_2$. Primary mouse RPE cells were isolated as previously described (Yang et al., 2009) and grown in Dulbecco Modified Eagle Medium (DMEM) supplemented with 20% FBS and standard antibiotics concentrations. Primary human RPE cells were isolated as previously described (Yang et al., 2008) and maintained in DMEM supplemented with 10% FBS and antibiotics. HeLa cells were maintained in DMEM supplemented with 20% FBS and standard antibiotics concentrations. THP-1 cells were cultured in RPMI 1640 medium supplemented with 10% FBS and antibiotics.

In Vitro Transcription of Alu RNAs.

Two Alu RNAs were synthesized: a 281 nt Alu sequence originating from the cDNA clone TS 103 (Shaikh et al., 1997) and a 302 nt Alu sequence isolated from the RPE of a human eye with geographic atrophy. Linearized plasmids containing these Alu sequences with an adjacent 5' T7 promoter were subjected to AmpliScribe™ T7-Flash™ Transcription Kit (Epicentre) according to the manufacturer's instructions. DNase-treated RNA was purified using MEGAclear™ (Ambion), and integrity was monitored by gel electrophoresis. This yields single stranded RNAs that fold into a defined secondary structure identical to Pol III derived transcripts. Where indicated, transcribed RNA was dephosphorylated using calf intestine alkaline phosphatase (Invitrogen) and repurified by Phenol:Chloroform:Isoamyl alcohol precipitation.

Transient Transfection.

Human or mouse RPE cells were transfected with pUC19, pAlu, pCDNA3.1/Dicer-FLAG, pCDNA3.1, Alu RNA, NLRP3 siRNA sense, PYCARD siRNA sense, MyD88 siRNA sense, DICER1 antisense oligonucleotide (AS), control (for DICER1) AS, Alu AS, and control (for Alu) AS using Lipofectamine 2000 (Invitrogen) according to the manufacturer's instructions.

Adenoviral Infection.

Cells were plated at density of $15\times10^3/cm^2$ and after 16 h, at approximately 50% confluence, were infected with AdCre or AdNull (Vector Laboratories) with a multiplicity of infection of 1,000.

Cell Viability.

MTS assays were performed using the CellTiter 96 AQueous One Solution Cell Proliferation Assay (Promega) according to the manufacturer's instructions. For examining the cytoprotective effect of glycine in Alu RNA induced cell death, human RPE cells were transfected with pNull/pAlu. At 6 h post-transfection the cells were incubated with complete media containing glycine (5 mM) or vehicle, and cell viability was assessed after 24 h. Similarly, human RPE cells primed with LPS (5 μg/ml for 6 h) were treated with ATP (25 μM) in the presence of glycine containing media (5 mM). 30 min post ATP cell viability was assessed as described above.

Caspase-1 Activity.

Caspase-1 activity was visualized by incubating cells with Caspalux1E1 D2 reagent (OncoImmunin) according to the manufacturer's instructions. Caspalux1E1D2 signal was quantified reading the fluorescence (excitation 552 nm, emission 580 nm) using a Synergy 4 reader (Biotek). Quantification of fluorescence from images was performed by converting images into grayscale in Adobe Photoshop CS5, and measuring the integrated density of black and white images using ImageJ software (NIH) (Bogdanovich et al., 2008).

Caspase-3 Activity.

The caspase-3 activity was measured using Caspase-3 Fluorimetric Assay (R&D Systems) according to the manufacturer's instruction.

ROS Activation.

Intracellular ROS was assessed using the ROS-specific probe 2'7'-dichlorodihydrofluorescin diacetate ($H_2DCFDA$, BioChemica, Fluka). Sub-confluent human RPE cells were transfected with pNull and pAlu. After 24 h cells were loaded for 10 min with 10 µM $H_2DCFDA$ and washed twice with PBS. Fluorescence was recorded in 96-well plate using with a Synergy 4 reader (Biotek) using a FITC filter (excitation 485 nm, emission 538 nm).

ELISA.

Secreted cytokine content in conditioned cell culture media was analyzed using the Human IL-1β and IL-18 ELISA Kits (R&D) according to the manufacturer's instructions.

TLR Screen.

A custom TLR ligand screen was performed by InvivoGen using HEK293 cells over-expressing individual TLR family members coupled with an AP-1/NF-κB reporter system. Cells were stimulated with each of two Alu RNAs synthesized by in vitro transcription, or a TLR-specific positive control ligand.

Statistical Analysis.

Results are expressed as mean±SEM, with p values <0.05 considered statistically significant. Differences between groups were compared by using Mann-Whitney U test or Student t-test, as appropriate, and 2-tailed p values are reported.

Results

Alu RNA does not Activate a Variety of TLRs or RNA Sensors.

Figure 2:
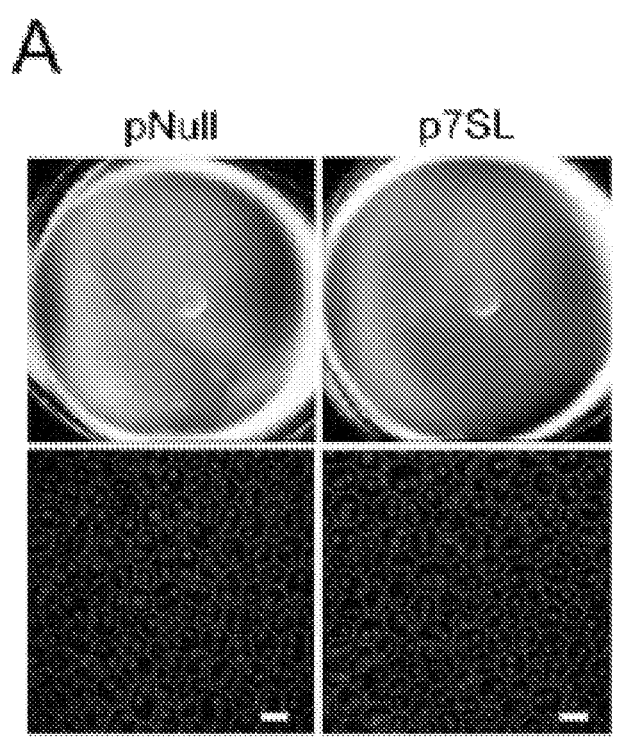
FIG. 2. Alu RNA does not activate several RNA sensors. (A and B) p7SL (a 7SL expression vector) (A) and in vitro synthesized 7SL RNA (B) do not induce RPE degeneration in wild-type mice. (C) RPE degeneration induced by subretinal injection of pAlu in wild-type mice is not blocked by a TLR4 antagonist. (D-E) Mice deficient in Mda5 (D) or Prkr (E) are susceptible to pAlu-induced RPE degeneration. (F) Dephosphorylated (Dep) Alu RNA induces RPE degeneration in wild-type mice just as well as Alu RNA. (G) Mice deficient in Mavs are susceptible to pAlu-induced RPE degeneration. pNull does not induce RPE degeneration in any strain of mice. Degeneration outlined by blue arrowheads. Fundus photographs, top rows; ZO-1 stained (red) RPE flat mounts, bottom rows. n=8 (A-G). (H) A schematic of the innate immune pathways that are not activated by Alu RNA.

Alu RNA has single-stranded (ss) RNA and double-stranded (ds) RNA motifs (Sinnett et al., 1991). Therefore, whether Alu RNA induced RPE degeneration in mice deficient in toll-like receptor-3 (TLR3), a dsRNA sensor (Alexopoulou et al., 2001), or in TLR7, a ssRNA sensor (Diebold et al., 2004; Heil et al., 2004) was tested. Subretinal administration of a plasmid coding for Alu RNA (pAlu) induced RPE degeneration in $Tlr3^{-/-}$ and $Tlr7^{-/-}$ mice just as in wild-type mice (FIGS. 1A-C). It has been shown that 21-nucleotide or longer fully complementary siRNAs can activate TLR3 on RPE cells (Kleinman et al., 2011). The lack of TLR3 activation by Alu RNA can be attributed to its complex structure containing multiple hairpins and bulges that might preclude it from binding TLR3. Neither 7SL RNA, the evolutionary precursor of Alu RNA that also has ssRNA and dsRNA motifs, nor p7SL induced RPE degeneration in wild-type mice (FIGS. 2A and 2B), suggesting that the cytotoxicity of Alu RNA might be due to as yet unclear structural features. pAlu induced RPE degeneration in Unc93b1 mutant mice (FIG. 1D), which are devoid of signaling from TLR3, TLR7, and TLR9 (Tabeta et al., 2006), indicating that these nucleic acid sensing TLRs are not activated by Alu RNA redundantly. pAlu administration also induced RPE degeneration in $Tlr4^{-/-}$ mice (FIG. 1E). Corroborating these data, the TLR4 antagonist *Rhodobacter sphaeroides* LPS (Qureshi et al., 1991) did not inhibit pAlu-induced RPE degeneration in wild-type mice (FIG. 2C). These data dismiss the possibility that TLR4-activating lipopolysaccharide contamination induced the observed RPE cell death. Furthermore, two different in vitro transcribed Alu RNAs (Kaneko et al., 2011) did not activate TLR-2, 3, 4, 5, 7, 8, or 9 in a reporter assay system based in human embryonic kidney 293 cells expressing each of the TLRs (FIG. 1F).

Because Alu RNA induced RPE degeneration independent of TLR activation, whether other dsRNA sensors such as melanoma-differentiation-associated gene 5 (MDA5, (Kato et al., 2006)) or protein kinase R (PKR, encoded by Prkr, (Yang et al., 1995)) might mediate Alu RNA toxicity was tested. However, pAlu induced RPE degeneration in both Mda5 and $Prkr^{-/-}$ mice (FIGS. 2D and 2E). The possibility was evaluated that the 5'-triphosphate on in vitro transcribed Alu RNA, which could potentially activate other immune sensors such as retinoic acid inducible gene I (RIG-I) or interferon-induced protein with tetratricopeptide repeats 1 (IFIT-1) that can sense this moiety (Hornung et al., 2006; Pichlmair et al., 2011), might be responsible for RPE degeneration. Dephosphorylated Alu RNA induced RPE degeneration in wild-type mice just as well as Alu RNA that had not been subjected to dephosphorylation (FIG. 2F), indicating that the presence of this chemical group is not responsible for the observed cell death in vivo. Indeed, it has been recently shown that a 5'-triphosphate ssRNA that activates RIG-I does not induce RPE degeneration in mice (Kleinman et al., 2011). Supportive of these findings, pAlu induced RPE degeneration in mice deficient in mitochondrial antiviral signaling protein (MAVS) (FIG. 2G), an adaptor protein through which RIG-I and MDA-5 signal (Kumar et al., 2006; Sun et al., 2006). Collectively these data pointed to a novel mechanism of Alu RNA-induced RPE degeneration not mediated by a wide range of canonical RNA sensors.

Alu RNA Cytotoxicity is Mediated Via MyD88 and IL-18.

Figure 3:
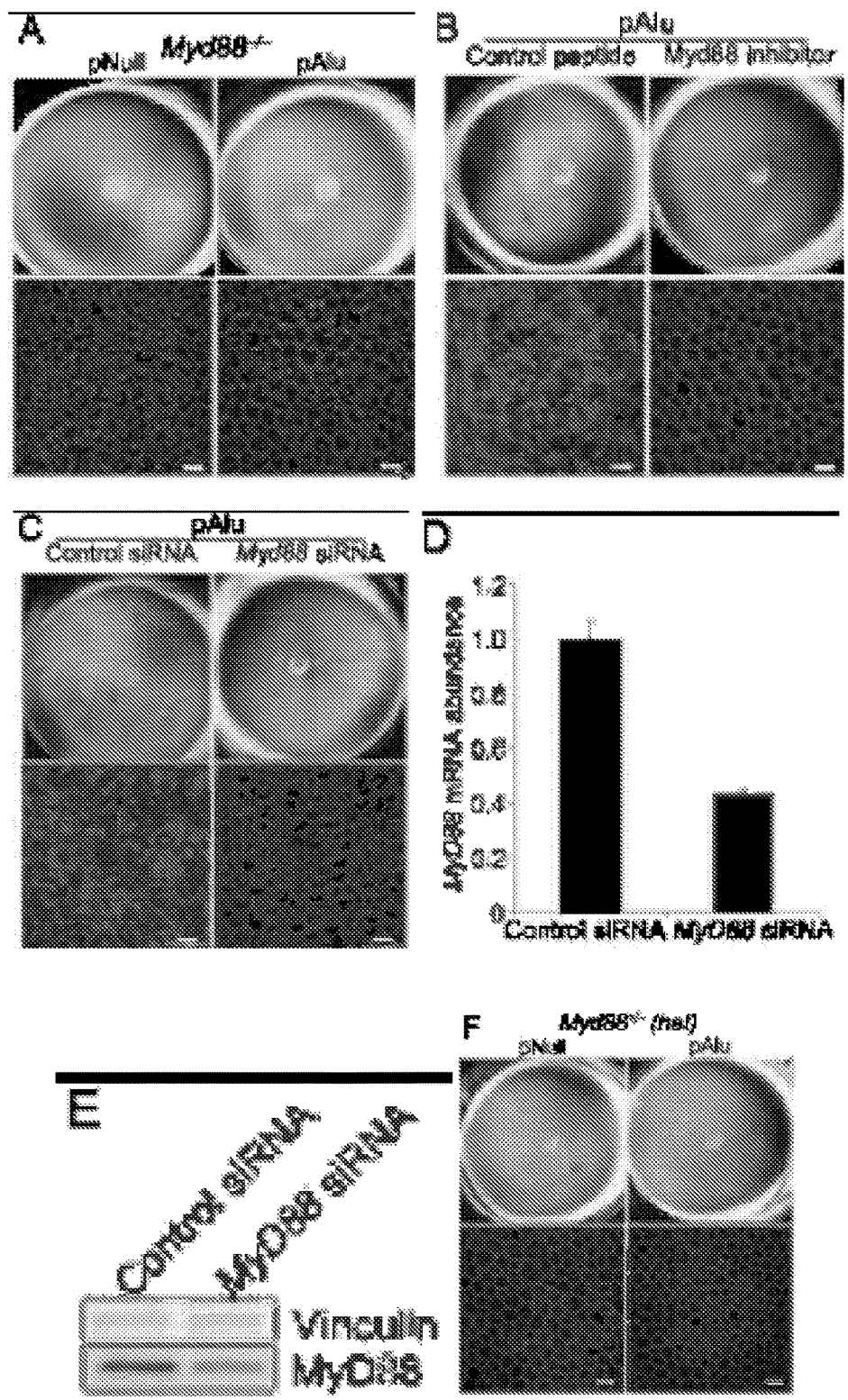
FIG. 3. Alu RNA induces RPE degeneration via MyD88. (A) pAlu does not induce RPE degeneration in Myd88$^{-/-}$ mice. (B) pAlu-induced RPE degeneration in wild-type mice is inhibited by a MyD88 homodimerization peptide inhibitor (MyD88i), but not by a control peptide. (C) pAlu-induced RPE degeneration in wild-type mice is inhibited by intravitreous cholesterol-conjugated Myd88 siRNA but not cholesterol-conjugated control siRNA. (D and E) siRNA targeting MyD88 (siMyD88) reduces target gene (D, real-time RT-PCR) and protein (E, western blotting normalized to Vinculin) abundance in mouse RPE cells compared to control siRNA transfection. n=3, *p<0.05 by Student t-test. (F) pAlu does not induce RPE degeneration in Myd88$^{+/-}$ heterozygous (het) mice. (G) Western blot of Alu RNA-induced phosphorylation of IRAK1 and IRAK4 in human RPE cells. Image representative of 3 experiments. (H) pAlu reduces cell viability of wild-type but not Myd88$^{-/-}$ mouse RPE cells. (I) Loss of human RPE cell viability induced by pAlu is rescued by MyD88i. (J) Subretinal injection of AAV1-BEST1-Cre, but not AAV1-BEST1-GFP, protected Myd88$^{f/f}$ mice from pAlu-induced RPE degeneration. (K) pAlu transfection induces IL-18 secretion from human RPE cells as assessed by ELISA. IL-1β secretion is barely detectable. n=3, *p<0.05 by Student t-test. (L) Intravitreous administration of recombinant IL-18 induces RPE degeneration in wild-type mice but not in Myd88$^{-/-}$ mice. (M and N) pAlu-induced RPE degeneration in wild-type mice is not rescued by intravitreous administration of IL-1β neutralizing antibody (M) but is rescued by IL-18 neutralizing antibody (N). Representative images shown. n=8-12. Fundus photographs, top row; ZO-1 stained (red) flat mounts, bottom row. Degeneration outlined by blue arrowheads. Scale bars, 20 μm (A-C, F, J, L-N). n=3, *p<0.05 by Student t-test. Error bars represent the SEM of samples within a group (D, E, H, I, K).
Figure 4:
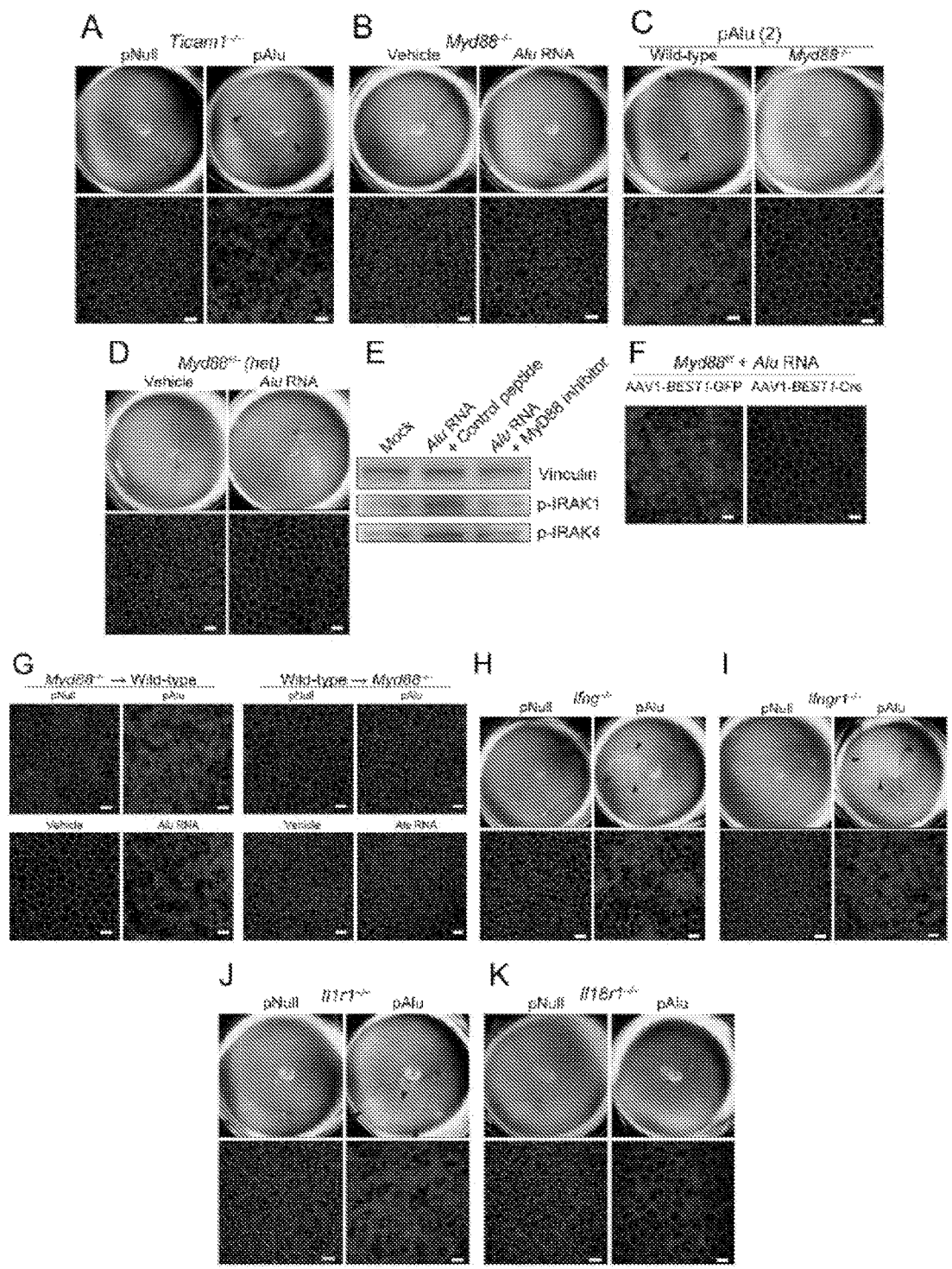
FIG. 4. Alu RNA induces RPE degeneration via MyD88, not TRIF or IFNγ. (A) Subretinal administration of pAlu induces RPE degeneration in Ticam1$^{-/-}$ mice. (B) Alu RNA does not induce RPE degeneration in Myd88$^{-/-}$ mice. (C) Subretinal administration of a different Alu expression plasmid (pAlu(2)) also induces RPE degeneration in wild-type but not Myd88$^{-/-}$ mice. (D) Alu RNA does not induce RPE degeneration in Myd88$^{+/-}$ heterozygous (het) mice. (E) MyD88 inhibitory peptide reduces Alu RNA-induced phosphorylation of IRAK¼, normalized to Vinculin expression. (F) Subretinal injection of AAV1-BEST1-Cre, but not AAV1-BEST1-GFP, protects Myd88$^{f/f}$ mice from Alu RNA-induced RPE degeneration. (G) pAlu and Alu RNA induces RPE degeneration in wild-type mice receiving Myd88$^{-/-}$ bone marrow (Myd88$^{-/-}$→wild-type) but did not do so in Myd88$^{-/-}$ mice receiving wild-type bone marrow (wild-type→Myd88$^{-/-}$). (H-K) Subretinal administration of pAlu induces RPE degeneration in Ifng$^{-/-}$ (H), Ifngr1$^{-/-}$ (I), and Il1r1$^{-/+}$ mice (J) but not in Il18r1$^{-/-}$ mice (K). pNull administration does not induce RPE degeneration in any strain of mice. Degeneration outlined by blue arrowheads. Fundus photographs, top rows; ZO-1 stained (red) RPE flat mounts, bottom rows. n=8 (A-D, F-K).

The potential involvement of TRIF (encoded by Ticam1), an adaptor protein for TLR3 and TLR4 was tested (Hoebe et al., 2003; Yamamoto et al., 2003), and myeloid differentiation primary response protein (MyD88), an adaptor protein for all TLRs except TLR3 was also tested (Akira et al., 2006; Alexopoulou et al., 2001; Suzuki et al., 2003). Subretinal administration of Alu RNA induced RPE degeneration in $Ticam1^{-/-}$ mice (FIG. 4A), consistent with the findings in $Tlr3^{-/-}$ and $Tlr4^{-/-}$ mice. Unexpectedly however, neither Alu RNA nor two different pAlu plasmids induced RPE degeneration in $Myd88^{-/-}$ mice (FIGS. 3A, 4B, and 4C). To corroborate these genetic findings, pharmacological inhibition of MyD88 was tested. Intravitreous administration of a peptide inhibitor of MyD88 homodimerization (Loiarro et al., 2005) prevented RPE degeneration induced by subretinal administration of Alu RNA in wild-type mice, whereas a control peptide did not impart protection (FIG. 3B). A MyD88-targeting short interfering RNA (siRNA) was tested, which was shorter than 21 nucleotides in length to prevent TLR3 activation and conjugated to cholesterol to enable cell permeation (Kleinman et al., 2008). MyD88 siRNA inhibited RPE degeneration induced by pAlu in wild-type mice, whereas a control siRNA did not do so (FIGS. 3C-3E). $Myd88^{+/-}$ heterozygous mice were protected against Alu RNA-induced RPE degeneration (FIGS. 3F and 4D), corroborating the findings from the siRNA studies that partial knockdown of MyD88 is therapeutically sufficient.

MyD88-mediated signal transduction induced by interleukins leads to recruitment and phosphorylation of the IL-1R-associated kinases IRAK1 and IRAK4 (Cao et al., 1996; Kanakaraj et al., 1999; Suzuki et al., 2003; Suzuki et al., 2002). Alu RNA increased phosphorylation of IRAK1/4 in human RPE cells (FIG. 3G), supporting the concept that Alu RNA triggers MyD88 signaling. The MyD88 inhibitory peptide reduced Alu RNA-induced phosphorylation of IRAK1/4 in human RPE cells (FIG. 4E), confirming its mechanism of action in this model.

Next it was assessed whether MyD88 activation mediates Alu RNA-induced cell death in human and mouse RPE cell culture systems. In congruence with the in vivo data, pAlu transfection reduced cell viability in wild-type but not Myd88$^{-/-}$ mouse RPE cells (FIG. 3H). The MyD88-inhibitory peptide, but not a control peptide, inhibited cell death in human RPE cells transfected with pAlu (FIG. 3I). Taken together, these data indicate that MyD88 is a critical mediator of Alu RNA-induced RPE degeneration.

MyD88 is generally considered an adaptor of innate immune cells (O'Neill and Bowie, 2007). However, Alu RNA induced cell death via MyD88 in RPE monoculture systems. Therefore, it was determined whether Alu RNA-induced RPE degeneration in mice was also dependent solely on MyD88 activation in RPE cells or whether it required MyD88 activation in innate immune cells. To determine the cell population that is critical for MyD88-dependent RPE cell death, "foxed" MyD88 mice were studied, as well as generated MyD88 bone marrow chimeras. Conditional ablation of MyD88 in the RPE by subretinal injection of AAV1-BEST1-Cre in Myd88$^{f/f}$ mice protected against Alu RNA-induced RPE degeneration (FIGS. 3J and 4F). Consistent with this finding, Alu RNA induced RPE degeneration in wild-type mice receiving Myd88$^{-/-}$ bone marrow but did not do so in Myd88$^{-/-}$ mice receiving wild-type bone marrow (FIG. 4G). Collectively, these results indicate that MyD88 expression in the RPE, and not in circulating immune cells, is critical for Alu RNA-induced RPE degeneration. These findings comport with histopathological studies of human GA tissue that show no infiltration of immune cells in the area of pathology (personal communication, C. A. Curcio, H. E. Grossniklaus, G. S. Hageman, L. V. Johnson).

Although MyD88 is critical in TLR signaling (O'Neill and Bowie, 2007), activation of MyD88 by Alu RNA appeared to be independent of TLR activation. Thus, other potential mechanisms of MyD88 involvement were examined. MyD88 can regulate interferon gamma (IFN-γ) signaling by interacting with IFN-γ receptor 1 (encoded by Ifngr1) (Sun and Ding, 2006). However, pAlu induced RPE degeneration in both Ifng$^{-/-}$ and Ifngr1$^{-/-}$ mice (FIGS. 4H and 4I). MyD88 is also essential in interleukin-1 (IL-1) signaling (Muzio et al., 1997). Therefore, it was tested whether IL-1β and the related cytokine IL-18, both of which activate MyD88 (Adachi et al., 1998), were involved in mediating Alu RNA cytotoxicity. Interestingly, whereas Alu RNA overexpression in human RPE cells increased IL-18 secretion, IL-1β secretion was barely detectable (FIG. 3K).

Recombinant IL-18 induced RPE degeneration in wild-type but not Myd88$^{-/-}$ mice (FIG. 3L). A neutralizing antibody against IL-18 protected against pAlu-induced RPE degeneration in wild-type mice, whereas IL-1β neutralization provided no benefit (FIGS. 3M and 3N). Supporting these findings, pAlu induced RPE degeneration in Il1r1$^{-/-}$ mice but not Il18r1$^{-/-}$ mice (FIGS. 4J and 4K). These data indicate that IL-18 is an important effector of Alu RNA-induced cytotoxicity.

Alu RNA activates the NLRP3 inflammasome.

Figure 5:
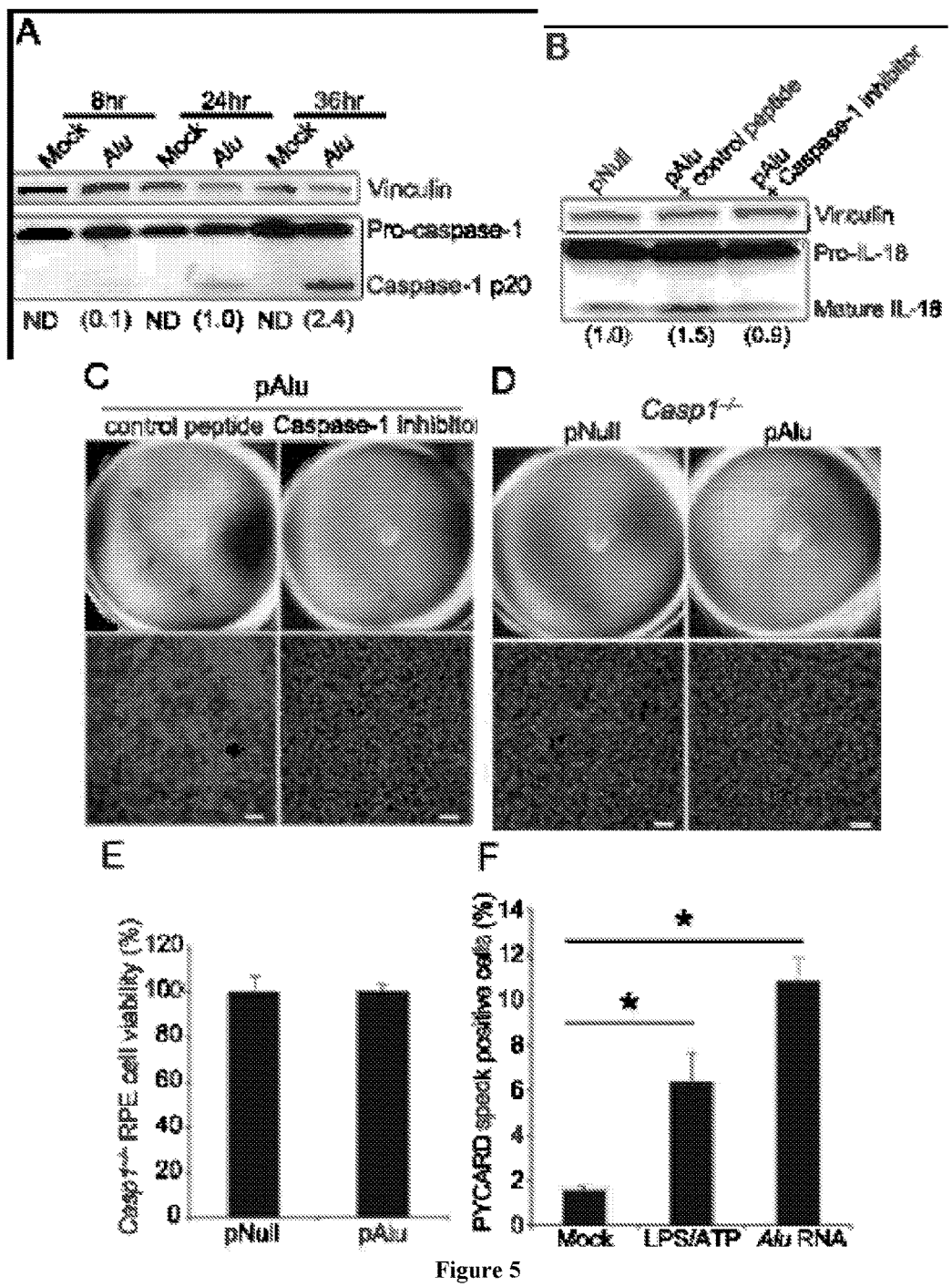
FIG. 5. Alu RNA induces RPE degeneration via NLRP3 inflammasome. (A) Western blot of Caspase-1 activation (p20 subunit) by Alu RNA in human RPE cells. (B) Western blot of pAlu-induced IL-18 maturation in RPE cell lysates in wild-type mice impaired by intravitreous Caspase-1 peptide inhibitor. (C) Intravitreous Caspase-1 peptide inhibitor protects wild-type mice from pAlu-induced RPE degeneration. (D) pAlu does not induce RPE degeneration in Casp1$^{-/-}$ mice. (E) pAlu does not induce cytotoxicity in Casp1$^{-/-}$ mouse RPE cells. (F) Alu RNA and LPS+ATP induce formation of PYCARD clusters in human RPE cells transfected with GFP-PYCARD. See also FIG. 6E. (G and H) pAlu does not induce RPE degeneration in Nlrp3$^{-/-}$ (G) or Pycard$^{-/-}$ (H) mice. (I) Nlrp3$^{-/-}$ and Pycard$^{-/-}$ mouse RPE cells are protected against pAlu-induced loss of cell viability. (J) siRNAs targeting NLRP3 or PYCARD rescued human RPE cells from pAlu-induced cytotoxicity, compared to control siRNA. n=3-4, *p<0.05 by Student t-test (A, B, E, F, I, J). Images representative of 3 experiments. Densitometry values normalized to Vinculin are shown in parentheses (A, B). Fundus photographs, top row; ZO-1 stained (red) flat mounts, bottom row. Degeneration outlined by blue arrowheads. n=8-12. Scale bars, 20 μm (C, D, G, H). Representative images shown.
Figure 6:
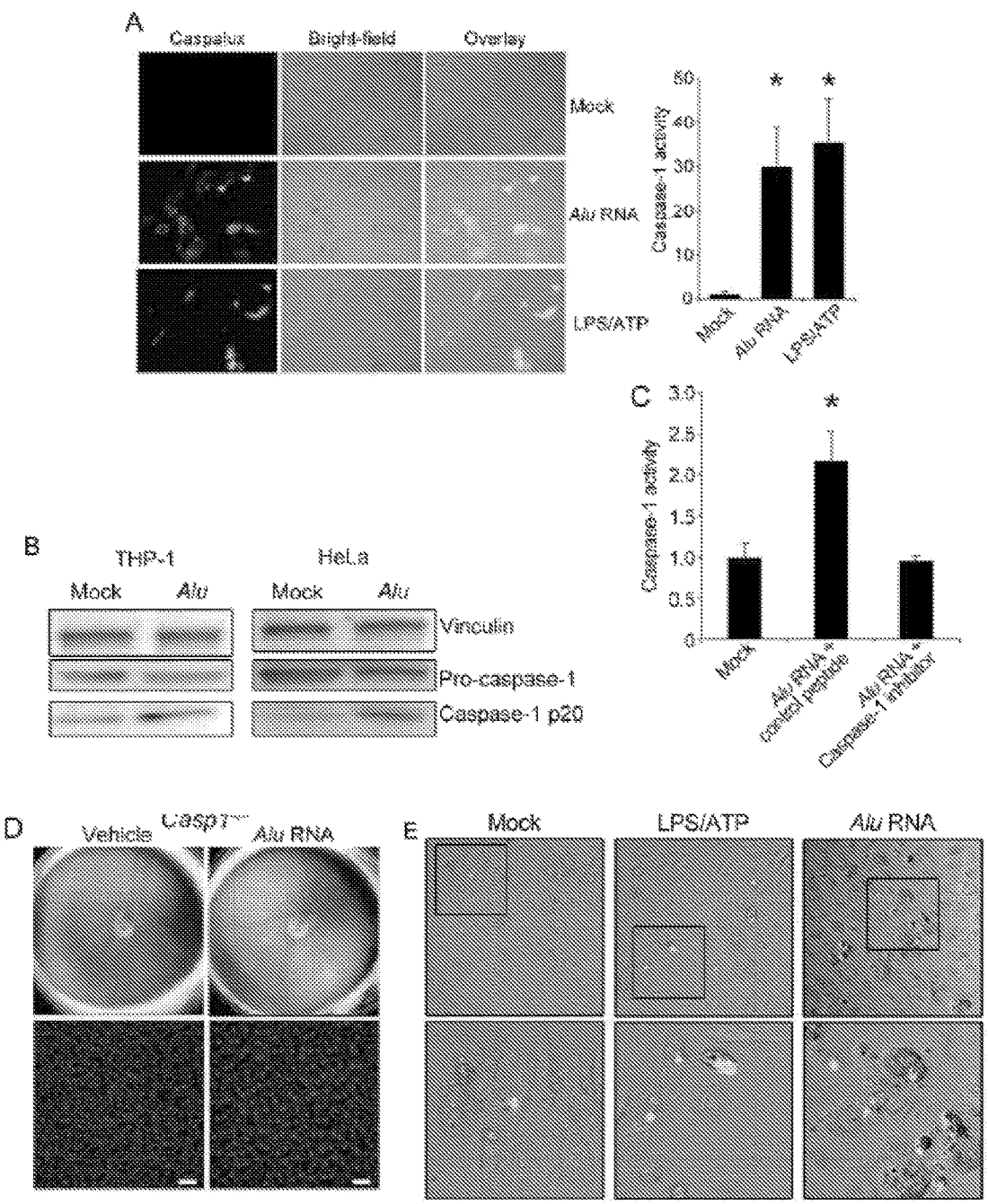
FIG. 6. Alu RNA induces RPE degeneration via NLRP3 inflammasome activation, Related to FIG. 7 (A) Alu RNA or LPS+ATP induce activation of Caspase-1 in human RPE cells as assessed by increased cleavage of Caspalux®1 (green, left panel), a fluorescent-linked peptide substrate as compared to mock treatment. Fluorescence quantification shown in right panel. (B) Western blot of Alu RNA-induced Caspase-1 activation (p20 subunit) in THP-1 and HeLa cells, normalized to Vinculin expression. (C) Caspase-1 inhibitor peptide blocks Alu RNA-induced substrate cleavage in human RPE cells. n=3. (D) Subretinal injection of Alu RNA does not induce RPE degeneration in Casp1$^{-/-}$ mice. (E) Alu RNA or LPS+ATP induce the appearance of a brightly fluorescent cluster of GFP-PYCARD visible in the cytoplasm of human RPE cells. Area in insets shown in higher magnification. Images representative of 3 experiments. (F and G) Subretinal injection of Alu RNA does not induce RPE degeneration in Nlrp3$^{-/-}$ (F) or Pycard$^{-/-}$ (G) mice. (H) The abundance of NLRP3 in HEK293 cells transfected with an NLRP3 expression vector and of PYCARD in human RPE cells is reduced by transfection of siRNAs targeting these genes, compared to control (Ctrl) siRNAs. n=3, *p<0.05 compared to Ctrl siRNAs by Student t-test. (I) Alu RNA-induced Caspase-1 activation (p20 subunit) in human RPE cells is unaffected by MyD88 inhibitory peptide, normalized to Vinculin expression. (J) MyD88 inhibitory peptide does not reduce Alu RNA-induced cleavage activity of Caspase-1 in human RPE cells (top panel). Fluorescence quantification (bottom panel). (K) Caspase-1 activation (p20 subunit) in RPE cell lysates of wild-type mice treated with subretinal pAlu administration is unimpaired by intravitreous administration of anti-IL-18 neutralizing antibodies. (L) Alu RNA-induced phosphorylation of IRAK1/4 is reduced by Caspase-1 inhibitory peptide in human RPE cells, normalized to Vinculin expression. Vehicle control injections also do not damage the RPE. Fundus photographs, top rows; ZO-1 stained (red) RPE flat mounts, bottom rows. n=8 (D, F, G). Images representative of 3 experiments (A, B, I, J-L).

Whether Caspase-1 (encoded by Casp1), a protease that can catalyze cleavage of the pro-forms of interleukins to their biologically active forms (Ghayur et al., 1997; Gu et al., 1997; Thornberry et al., 1992), was involved in Alu RNA-induced RPE degeneration was explored. Alu RNA treatment of human RPE cells led to Caspase-1 activation as measured by western blot analysis and by a fluorescent reporter of substrate cleavage (FIGS. 5A and 6A). Indeed, Alu RNA induced Caspase-1 activation in other cell types such as HeLa and THP-1 monocytic cells (FIG. 6B), suggesting that the cytotoxicity of Alu RNA has potentially broad implications in many systems. Intravitreous administration of the Caspase-1-inhibitory peptide Z-WEHD-FMK, but not a control peptide Z-FA-FMK, blocked IL-18 maturation and pAlu-induced RPE degeneration in wild-type mice (FIGS. 5B and 5C). The Caspase-1-inhibitory peptide blocked Alu RNA-induced substrate cleavage in human RPE cells (FIG. 6C), confirming its mechanism of action in this system. These findings were corroborated by the absence of RPE degeneration in Casp1$^{-/-}$ mice treated with Alu RNA or pAlu (FIGS. 5D and 6D). Also, pAlu did not induce cell death in Casp1$^{-/-}$ mouse RPE cells (FIG. 5E).

Caspase-1 can be activated within a multiprotein innate immune complex termed the inflammasome (Tschopp et al., 2003). The best-characterized inflammasome pathway is one that is activated by binding of NLRP3 (nucleotide-binding domain, leucin-rich-containing family, pyrin domain-containing-3) to the caspase-1 adaptor apoptosis-associated speck-like protein containing a caspase-recruitment domain (ASC; encoded by PYCARD).

To assess whether Alu RNA induced inflammasome assembly, human RPE cells were transfected with a vector encoding a fusion protein of PYCARD and green fluorescent protein (GFP-PYCARD), which enabled spatial clustering of PYCARD that occurs upon PYCARD activation in cell culture to be optically-monitored (Fernandes-Alnemri et al., 2007). Alu RNA induced the appearance of a brightly fluorescent cluster of GFP-PYCARD visible in the cytoplasm similar to treatment with LPS and ATP, which is known to activate the NLRP3 inflammasome (FIGS. 5F and 6E) (Mariathasan et al., 2006).

Next the functional relevance of NLRP3 and PYCARD to Alu RNA cytotoxicity was tested using genetic and pharmacological inhibition. Neither pAlu nor Alu RNA induced RPE degeneration in either Nlrp3$^{-/-}$ or Pycard$^{-/-}$ mice (FIGS. 5G, 5H, 6F and 6G), demonstrating the critical importance of the inflammasome in transducing the cytotoxicity of Alu RNA. It was also found that pAlu did not induce cell death in Nlrp3$^{-/-}$ or Pycard$^{-/-}$ mouse RPE cells (FIG. 5I). Moreover, knockdown of NLRP3 or PYCARD by siRNAs rescued pAlu-induced human RPE cell death (FIGS. 5J and 6H). These findings provide direct evidence that NLRP3 activation in response to Alu RNA occurs in RPE cells and does not require the presence of other immune cells.

It was determined that IL-18 and MyD88 activation indeed were downstream of Caspase-1 activation by showing (1) that whereas the MyD88 inhibitory peptide reduced Alu RNA-induced phosphorylation of IRAK1/4 in human RPE cells (FIG. 4E), it did not reduce Alu RNA-induced Caspase-1 cleavage or fluorescent substrate cleavage (FIGS. 6I and 6J); (2) that IL-18 neutralizing antibodies did not inhibit Alu RNA-induced Caspase-1 cleavage (FIGS. 6K); and (3) that the Caspase-1 inhibitory peptide reduced Alu RNA-induced phosphorylation of IRAK1/4 (FIG. 6L).

Figure 7:
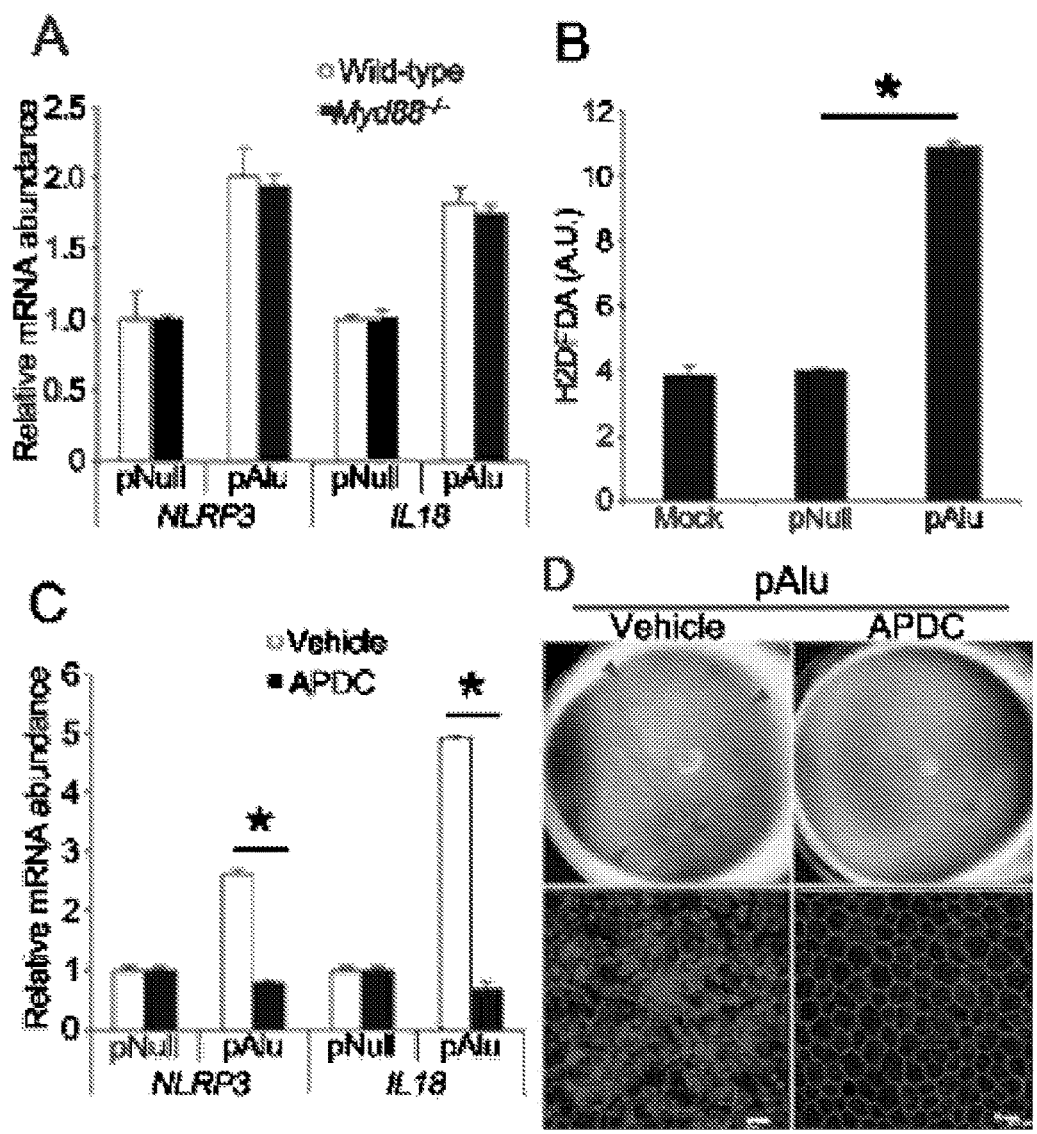
FIG. 7. Priming and activation of NLRP3. (A) pAlu induces NLRP3 and IL18 mRNAs in both wild-type and Myd88$^{-/-}$ mouse RPE cells. (B) pAlu induces generation of reactive oxygen species (ROS) in human RPE cells as monitored with the fluorescent probe H$_2$DCFDA (A.U, arbitrary units). (C) The ROS inhibitor APDC blocks pAlu-induced NLRP3 and IL18 mRNAs in human RPE cells. (D) Intravitreous administration of APDC protects wild-type mice from pAlu-induced RPE degeneration. (E) pAlu does not induce RPE degeneration in P2rx7$^{-/-}$ mice. (F) Intravitreous administration of P2X$_7$ receptor antagonist protects wild-type mice from pAlu-induced RPE degeneration. (G) Intravitreous administration of glyburide, but not glipizide, protects wild-type mice from pAlu-induced RPE degeneration. n=3-4, *p<0.05 by Student t-test (A-C). Representative images shown. n=8-12. Fundus photographs, top row; ZO-1 stained (red) flat mounts, bottom row. Degeneration outlined by blue arrowheads. Scale bars, 20 μm (D-G).

NLRP3 inflammasome function is thought to require two signals, the first of which is termed priming. pAlu induced inflammasome priming as it upregulated both NLRP3 and IL18 mRNAs. This priming occurred equivalently in both wild-type and Myd88$^{-/-}$ mouse RPE cells (FIG. 7A), further corroborating that MyD88 functions downstream of NLRP3 in this system. pAlu induced the generation of reactive oxygen species (ROS) (FIG. 7B), a signal for NLRP3 priming (Bauernfeind et al., 2011; Nakahira et al., 2011), and the ROS inhibitor APDC blocked pAlu-induced NLRP3 and IL18 mRNA upregulation (FIG. 7C). Consistent with these data, APDC blocked pAlu-induced RPE degeneration in wild-type mice (FIG. 7D).

NLRP3 inflammasome activation is also known to involve the ATP-gated channel $P2X_7$ (encoded by P2RX7), whose activation leads to cellular efflux of $K^+$ (Mariathasan et al., 2004). As disclosed herein, $P2rx7^{-/-}$ mice were protected against pAlu-induced RPE degeneration and the $P2X_7$ receptor antagonist A438079 blocked pAlu-induced RPE degeneration in wild-type mice (FIGS. 7E and 7F). Consonant with these data, pAlu-induced RPE degeneration in wild-type mice was inhibited by glyburide, which functions downstream of $P2X_7$ to block NLRP3 activation (Lamkanfi et al., 2009), but not by the closely related glipizide, which does not block NLRP3 (FIG. 7G).

IL-18 and MyD88 Induces RPE Degeneration Via Caspase-3.

Figure 8:
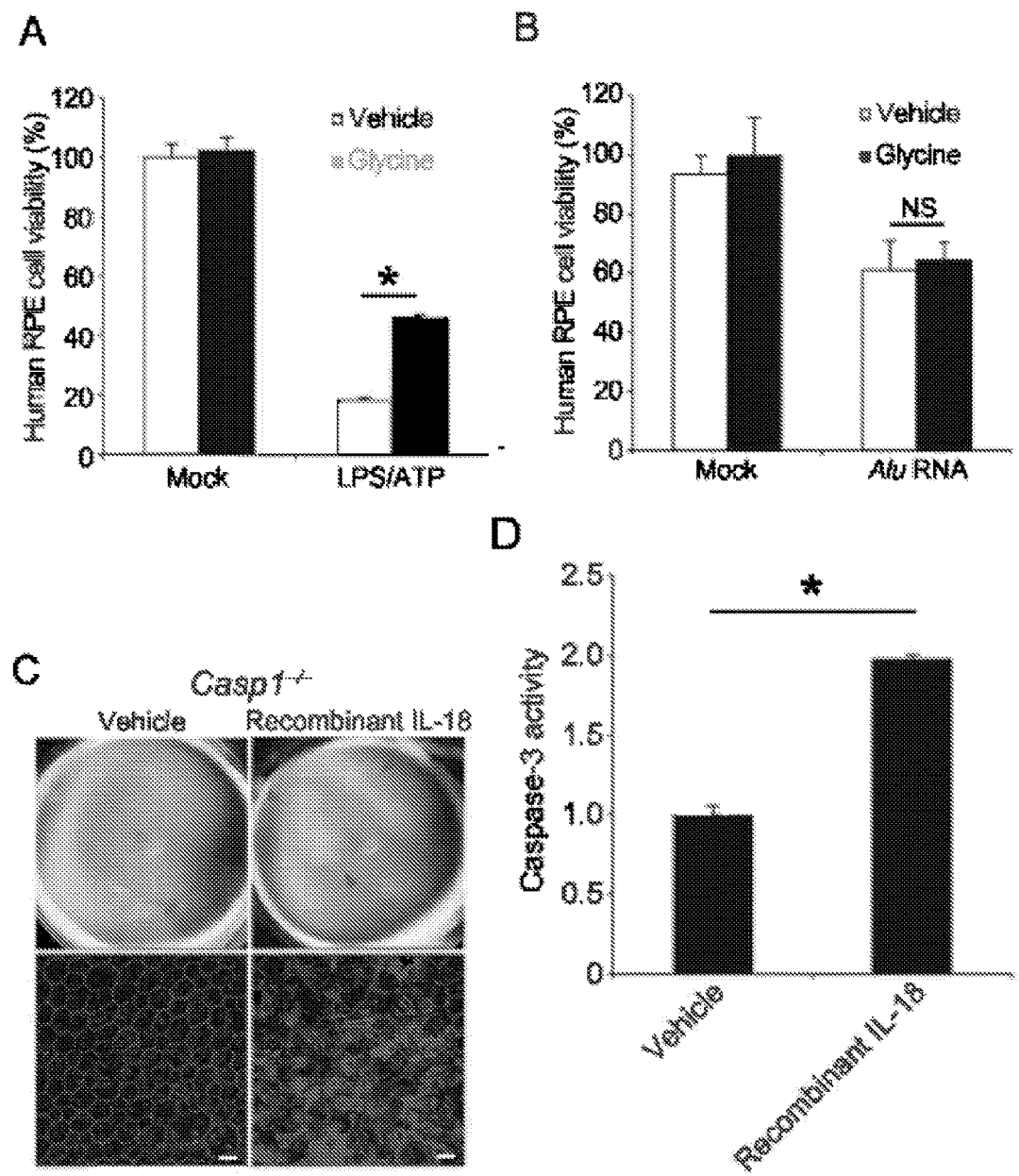
FIG. 8. IL-18 and MyD88 induce RPE degeneration via Caspase-3. (A and B) Glycine inhibits human RPE cell death induced by LPS+ATP (A) but not by pAlu (B). (C) Intravitreous administration of recombinant IL-18 induces RPE degeneration in Casp1$^{-/-}$ mice. (D) IL-18-induced activation of Caspase-3 in RPE cell lysates of wild-type mice. (E) IL-18-induced RPE degeneration in wild-type mice is inhibited by intravitreous administration of Caspase-3 inhibitor. (F) Intravitreous administration of MyD88 inhibitory peptide inhibits pAlu-induced cleavage of Caspase-3 in the RPE of wild-type mice. n=3-4 (A, B, D, F), *p<0.05 by Student t-test. Representative images shown. n=8-12. Fundus photographs, top row; ZO-1 stained (red) flat mounts, bottom row. Degeneration outlined by blue arrowheads. Scale bars, 20 μm (C, E).

The mode of cell death in Alu RNA-induced RPE degeneration mediated via IL-18 activation of MyD88 was sought to be determined. Alu RNA activates Caspase-1, which can trigger pyroptosis, a form of cell death characterized by formation of membrane pores and osmotic lysis (Fink and Cookson, 2006). It was found that the cytoprotective agent glycine, which can attenuate pyroptosis (Fink et al., 2008; Fink and Cookson, 2006; Verhoef et al., 2005), inhibited human RPE cell death induced by LPS+ATP but not by Alu RNA (FIGS. 8A and 8B). Pyroptosis requires Caspase-1 but can proceed independent of IL-18 (Miao et al., 2010). Therefore, the finding that IL-18 induced RPE degeneration in $Casp1^{-/-}$ mice (FIG. 8C), coupled with the lack of rescue by glycine, suggests that Alu RNA-induced RPE degeneration does not occur via pyroptosis.

It was reported earlier that Alu RNA activates Caspase-3 (Kaneko et al., 2011), an executioner protease associated with apoptosis. In wild-type mice, IL-18 induced Caspase-3 activation in the RPE (FIG. 8D), and the Caspase-3 inhibitor Z-DEVD-FMK blocked IL-18-induced RPE degeneration (FIG. 8E). Because IL-18 induces RPE degeneration in mice via MyD88, it was tested whether MyD88 inhibition also blocks Caspase-3 activation. Indeed, the MyD88 inhibitory peptide inhibited Alu RNA-induced Caspase-3 activation in the RPE of wild-type mice (FIG. 8F). Collectively, these data point towards apoptosis as the mode of cell death in Alu RNA-induced RPE degeneration, and are consistent with other systems wherein IL-18 and MyD88 induce apoptosis (Aliprantis et al., 2000; Chandrasekar et al., 2004; Ohtsuki et al., 1997). These findings are also compatible with the observations of Caspase-3 activation (Kaneko et al., 2011) and apoptosis (Dunaief et al., 2002) in RPE cells in human GA.

DICER1 Loss Induces Cell Death Via Inflammasome.

Figure 10:
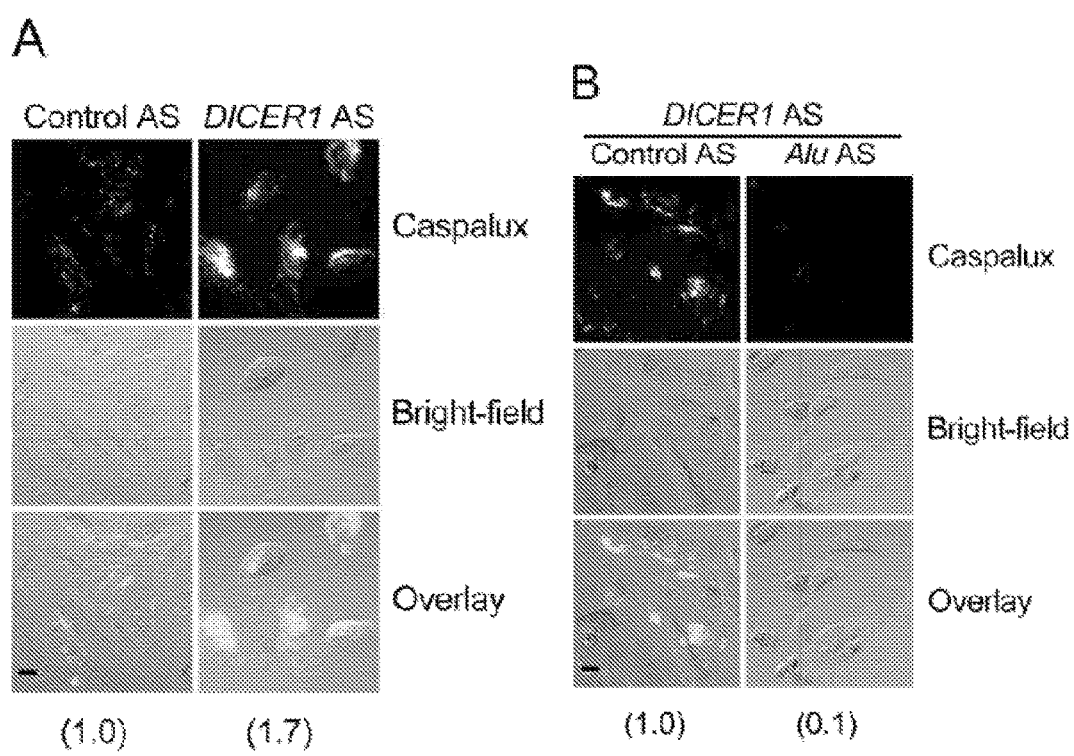
FIG. 10. DICER1 is a negative regulator of Caspase-1 activation by Alu RNA, Related to FIG. 9 (A) Knockdown of DICER1 by antisense oligonucleotides (AS) in human RPE cells increases cleavage activity of Caspase-1, as monitored by Caspalux, a fluorescent (green in overlay) reporter of substrate cleavage compared to control AS treatment. (B) Inhibition of Alu RNA by AS treatment reduces Caspalux fluorescence in human RPE cells treated with DICER1 AS. Mean values of Caspalux fluorescence shown in parentheses. Images representative of 3 experiments.

It has been demonstrated that the key role of DICER1 in maintaining RPE cell health (Kaneko et al., 2011): DICER1-cleaved Alu RNA did not induce RPE degeneration in vivo; DICER1 overexpression protected against Alu RNA-induced RPE degeneration; and DICER1 loss-induced RPE degeneration was blocked by antisense oligonucleotides targeting Alu RNA (Kaneko et al., 2011). Also, rescue of DICER1 knockdown-induced RPE degeneration by Alu RNA inhibition was not accompanied by restoration of microRNA deficits (Kaneko et al., 2011). Therefore, it was tested whether DICER1 also prevented NLRP3 inflammasome activation by Alu RNA. Alu RNA-induced Caspase-1 activation in human RPE cells, as monitored by western blot analysis and by a fluorescent reporter of substrate cleavage, was inhibited by DICER1 overexpression (FIGS. 6A and 6B). Conversely, Caspase-1 cleavage induced by DICER1 knockdown in human RPE cells, as monitored by immunofluorescence assay, was inhibited by simultaneous antisense-mediated knockdown of Alu RNA (FIGS. 10A and 10B).

Figure 9:
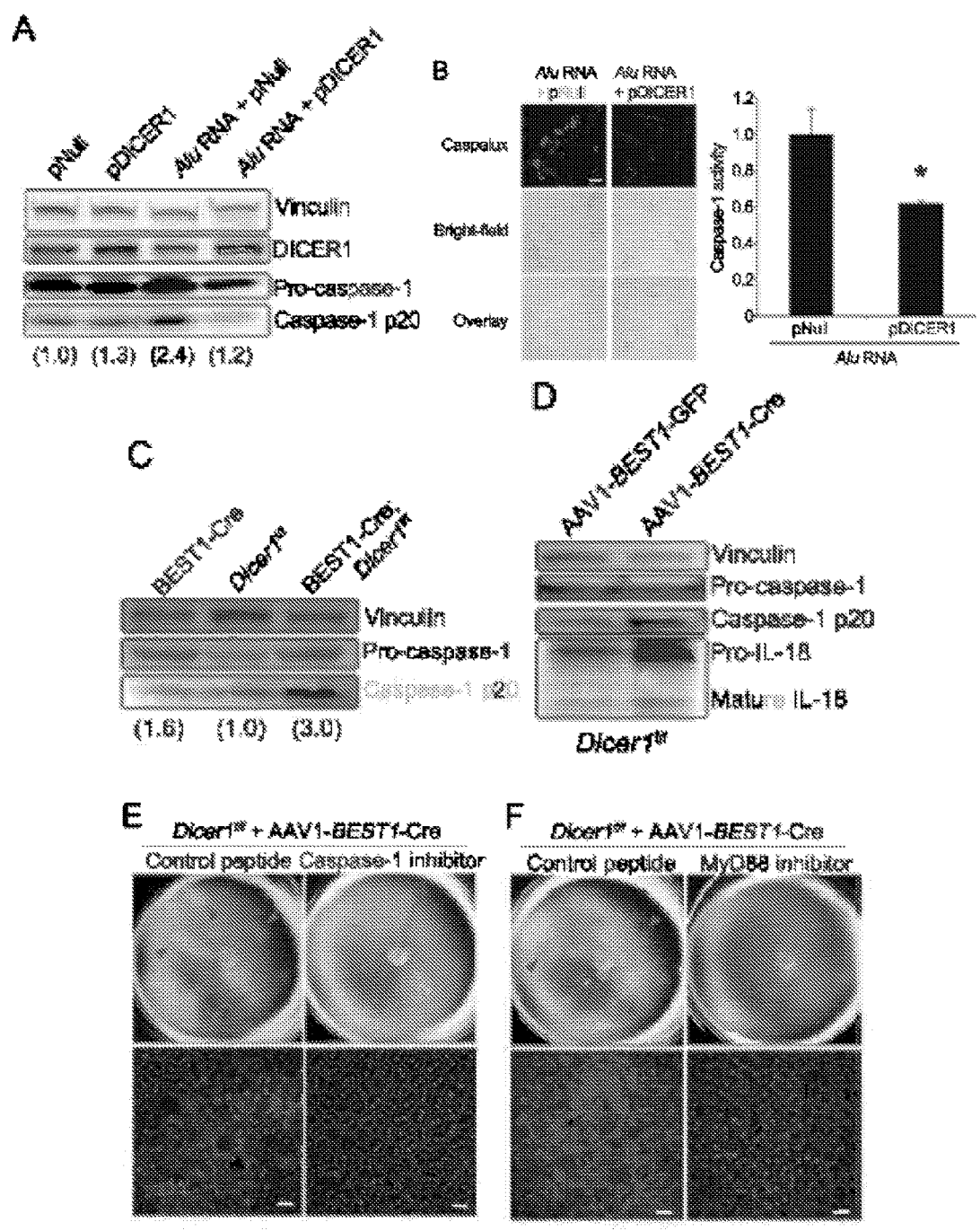
FIG. 9. DICER1 loss induces cell death via inflammasome. (A) Western blot of Alu RNA-induced Caspase-1 cleavage (p20) inhibited by DICER1 overexpression in human RPE cells. (B and C) DICER1 overexpression reduces Alu RNA-induced Caspase-1 activation in human RPE cells (measured by cleavage (B left panel, green) of Caspalux®1 fluorescent substrate). Fluorescence quantification shown in right panel. (C) Western blot of increased Caspase-1 activation (p20 subunit) in RPE cell lysates of BEST1-Cre; Dicer1$^{f/f}$ mice compared to BEST1-Cre or Dicer1$^{f/f}$ mice. (D) Western blot of increased Caspase-1 activation (p20 subunit) and IL-18 maturation in RPE cell lysates of Dicer1$^{f/f}$ mice treated with subretinal injection of AAV1-BEST1-Cre. (E and F) RPE degeneration induced by subretinal injection of AAV1-BEST1-Cre in Dicer1$^{f/f}$ mice is rescued by intravitreal delivery of peptide inhibitors of either Caspase-1 (E) or MyD88 (F). (G) MyD88 inhibitor rescues loss of human RPE cell viability induced by DICER1 antisense (AS) treatment. (H) DICER1 antisense (AS) treatment of human RPE cells reduces DICER1 level and increases abundance of phosphorylation of IRAK1 and IRAK4, normalized to Vinculin expression. (I) MyD88 inhibitor rescues loss of cell viability in Dicer1$^{f/f}$ mouse RPE cells treated with adenoviral vector coding for Cre recombinase (Ad-Cre). (J) Ad-Cre induced global miRNA expression deficits in Dicer1$^{f/f}$ mouse RPE cells compared to Ad-Null. No significant difference in miRNA abundance between MyD88 inhibitor and control peptide-treated Dicer' depleted cells. n=3 (A, B, F-H). Densitometry values normalized to Vinculin are shown in parentheses (A, C). Degeneration outlined by blue arrowheads. n=8 (E, F). *p<0.05 by Student t-test (G, I). Images representative of 3 experiments (A, B, C, D, H).

Next the in vivo functional relevance of these pathways was tested in the context of DICER1 loss in vivo. Caspase-1 cleavage was increased in the RPE of BEST1 Cre; $Dicer1^{f/f}$ mice (FIG. 9C), which lose DICER1 expression in the RPE during development and exhibit RPE degeneration (Kaneko et al., 2011). Subretinal delivery of AAV1-BEST1-Cre in $Dicer1^{f/f}$ mice induced Caspase-1 activation and IL-18 maturation in the RPE (FIG. 9D). This treatment also induced RPE degeneration, which was blocked by intravitreous administration of the Caspase-1-inhibitory peptide but not the control peptide (FIG. 9E). AAV1-BEST1-Cre-induced RPE degeneration in $Dicer1^{f/f}$ mice was also blocked by intravitreous administration of the MyD88-inhibitory peptide but not a control peptide (FIG. 9F). In addition, the MyD88-inhibitory peptide prevented cell death in human RPE cells treated with antisense oligonucleotides targeting DICER1 (FIG. 9G). DICER1 knockdown in human RPE cells increased phosphorylation of IRAK1/4, providing further evidence of MyD88 activation upon loss of DICER1 (FIG. 9H). The MyD88-inhibitory peptide also prevented cell death in $Dicer1^{f/f}$ mouse RPE cells treated with an adenoviral vector coding for Cre recombinase (FIG. 9I). MyD88 inhibition blocked RPE cell death without restoring the microRNA expression deficits induced by Dicer1 knockdown (FIG. 9J). These findings demonstrate that DICER1 is an essential endogenous negative regulator of NLRP3 inflammasome activation, and that DICER1 deficiency leads to Alu RNA-mediated, MyD88-dependent, microRNA-independent RPE degeneration.

Inflammasome and MyD88 Activation in Human GA.

Figure 11:
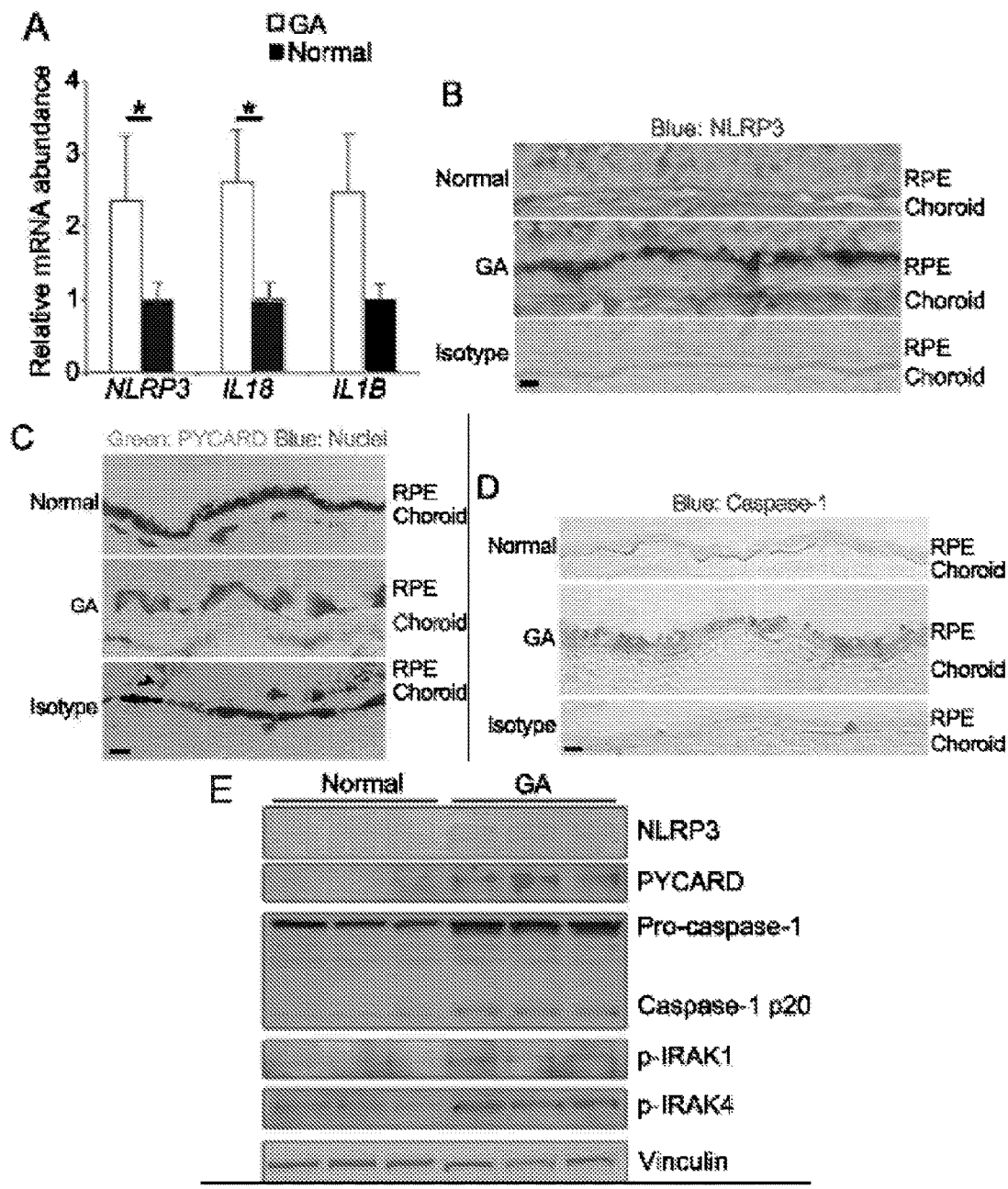
FIG. 11. NLRP3 Inflammasome and MyD88 activation in human GA. (A) NLRP3 and IL18 abundance was significantly elevated in macular GA RPE (n=13) compared to normal age-matched controls (n=12). *p<0.05 by Mann-Whitney U-test. There was no significant difference between groups (p=0.32 by Mann-Whitney U-test) in IL1B abundance. (B-D) Increased immunolocalization of NLRP3 (B), PYCARD (C) and Caspase-1 (D) in macular GA RPE compared to age-matched normal controls. Specificity of staining confirmed by absence of reaction production with isotype control antibody in GA eye sections. Scale bar, 20 µm. (E) Western blots of macular RPE lysates from individual human donor eyes show that abundance of NLRP3, PYCARD, and phosphorylated IRAK1/4 (which are activated by MyD88 signaling), normalized to the levels of the housekeeping protein Vinculin, is reduced in geographic atrophy (GA) compared to age-matched normal controls. Representative images shown. n=6 (B-E).

Next, it was determined whether human eyes with GA, which exhibit loss of DICER1 and accumulation of Alu RNA in their RPE (Kaneko et al., 2011), also display evidence of inflammasome activation. The abundance of NLRP3 mRNA in the RPE of human eyes with GA was markedly increased compared to control eyes (FIG. 11A), as monitored by real-time RT-PCR. IL18 and IL1B mRNA abundance also was increased in GA RPE; however, only the disparity in IL18 levels reached statistical significance (FIG. 11A). Immunolocalization studies showed that the expression of NLRP3, PYCARD, and Caspase-1 proteins was also increased in GA RPE (FIGS. 11B-D). Western blot analyses corroborated the increased abundance of NLRP3 and PYCARD in GA RPE, and revealed greatly increased levels of the enzymatically active cleaved Caspase-1 p20 subunit in GA RPE (FIG. 11E). There was also an increase in the abundance of phosphorylated IRAK1 and IRAK4 in GA RPE, indicative of increased MyD88 signal transduction (FIG. 11E). Collectively, these data provide evidence of NLRP3 inflammasome and MyD88 activation in situ in human GA, mirroring the functional data in human RPE cell culture and mice in vivo.

DISCUSSION

The data presented herein establish a functional role for the subversion of innate immune sensing pathways by repetitive element transcripts in the pathogenesis of GA. Collectively, the findings demonstrate that the NLRP3 inflammasome senses GA-associated Alu RNA danger signals, contributes to RPE degeneration, and potentially vision loss in AMD. To date, the function of the NLRP3 inflammasome has been largely restricted to immune cells in vivo. The finding that it plays a critical function in RPE cell survival broadens the cellular scope of this inflammasome and raises the possibility that other non-immune cells could employ this platform.

The NLRP3 inflammasome was originally recognized as a sensor of external danger signals such as microbial toxins (Kanneganti et al., 2006; Mariathasan et al., 2004; Mariathasan et al., 2006; Muruve et al., 2008). Subsequently, endogenous crystals, polypeptides, and lipids were reported to activate it in diseases such as gout, atherogenesis, Alzheimer disease, and Type 2 diabetes (Halle et al., 2008; Masters et al., 2010: Muruve et al, 2008; Vandanmagsar et al., 2011; Wen et al, 2011). To the Applicant's knowledge, Alu RNA is the first endogenous nucleic acid known to activate this immune platform. The findings disclosed herein expand the diversity of endogenous danger signals in chronic human diseases, and comport with the concept that this inflammasome is a sensor of metabolic danger (Schroder et al., 2010).

Dampening inflammasome activation can be essential to limiting the inflammatory response. Pathogens have evolved many strategies to inhibit inflammasome activation (Maranon et al., 2009). Likewise, host autophagy proteins (Nakahira et al., 2011; Saitoh et al., 2008), Type I interferon (Guarda et al., 2011), and T cell contact with macrophages can inhibit this process (Guarda et al., 2009). The finding that DICER1, through its cleavage of retrotransposon transcripts, prevents activation of the NLRP3 inflammasome adds to the repertoire of host inflammasome modulation capabilities and reveal a new facet of how dysregulation of homeostatic anti-inflammatory mechanisms can promote AMD (Ambati et al., 2003; Takeda et al., 2009).

Added to its recently described anti-apoptotic and tumor-related functions, DICER1 emerges as a multifaceted protein. It remains to be determined how this functional versatility is channeled in various states. As DICER1 dysregulation is increasingly recognized in several human diseases, it is reasonable to imagine that Alu RNA might be an inflammasome activating danger signal in those conditions too. It is also interesting that, at least in adult mice and in a variety of mouse and human cells, the microRNA biogenesis function of DICER1 is not critical for cell survival, at least in a MyD88-deficient environment (data not shown).

Although DICER1 levels are important in maintaining RPE cell health by metabolizing Alu RNA, other nucleases also may regulate Alu RNA. For example, Alu is a retrotransposon that can form RNA-DNA replication intermediates, which would be substrates for RNase H. Indeed, RNase H inhibits retrotransposition (Ma and Crouch, 1996), and human enzymes such as LINE-1 (Dhellin et al., 1997; McClure, 1991) contain an RNase H domain. The Argonaute-related PIWI family of nucleases (Parker et al., 2004) also contain an RNase H domain, though it is not known whether the human homolog HIWI degrades retrotransposon intermediates. Other enzymes such as the PIWI-related MIWI in mice also directly cleave retrotransposon RNA (Reuter et al., 2011). Thus, it is likely that DICER1 is one of several mechanisms by which cells regulate retrotransposon expression.

Current clinical programs targeting the inflammasome largely focus on IL-1β; presently there are no IL-18 inhibitors in registered clinical trials. However, the data indicate that IL-18 is more important than IL-1β in mediating RPE cell death in GA (similar to selective IL-18 involvement in a colitis model (Zaki et al., 2010)), pointing to the existence of as yet unknown regulatory mechanisms by which inflammasome activation bifurcates at the level of or just preceding the interleukin effectors. Although Caspase-1 inhibition could be an attractive local therapeutic strategy, caspase inhibitors can promote alternative cell death pathways, possibly limiting their utility (Vandenabeele et al., 2006).

Figure 12:
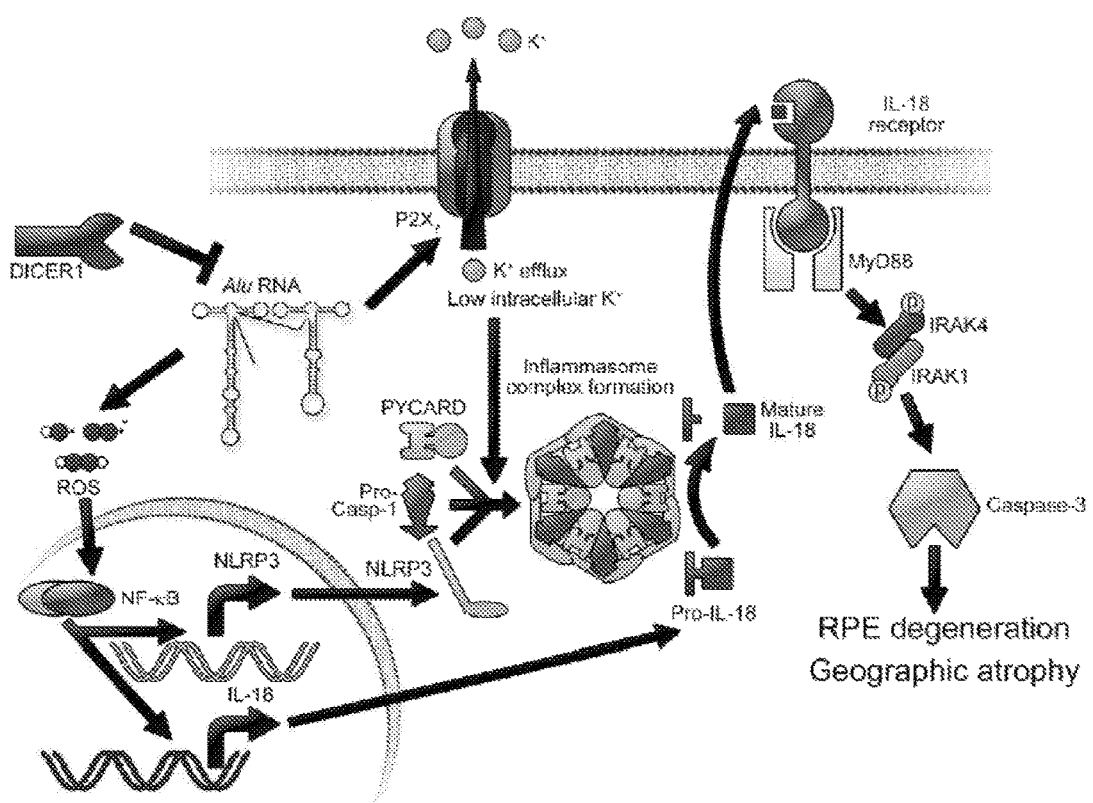
FIG. 12, Schematic representation of proposed model of NLRP3 inflammasome activation by DICER1 deficit-induced Alu RNA that leads to RPE degeneration and geographic atrophy. Alu RNA induces priming of NLRP3 and IL18 mRNAs via generation of reactive oxygen species (ROS). Alu RNA activates the NLRP3 inflammasome via P2X7 activation. This triggers cleavage of pro-IL-18 by activated Caspase-1 to mature IL-18. IL-18 signals via MyD88 to phosphorylate IRAK1 and IRAK4, which leads to activation of Caspase-3.

MyD88 is best known for transducing TLR signaling initiated by pathogen associated molecular patterns (O'Neill and Bowie, 2007), although recently it has been implicated in human cancers (Ngo et al., 2011; Puente et al., 2011; Rakoff-Nahoum and Medzhitov, 2007). The findings introduce an unexpected new function for MyD88 in effecting death signals from mobile element transcripts that can lead to retinal degeneration and blindness, and raise the possibility that MyD88 could be a central integrator of signals from other non-NLRP3 inflammasomes that also employ Caspase-1 (Schroder and Tschopp, 2010). Since non-canonical activation of MyD88 is a critical checkpoint in RPE degeneration in GA (FIG. 12), it represents an enticing therapeutic target. A potential concern is its important antimicrobial function in mice (O'Neill and Bowie, 2007). However, in contrast to Myd88$^{-/-}$ mice, adult humans with MyD88 deficiency are described to be generally healthy and resistant to a wide variety of microbial pathogens (von Bernuth et al., 2008). MyD88-deficient humans have a narrow susceptibility range to pyogenic bacterial infections, and that too only in early childhood and not adult life (Picard et al., 2010). Moreover, as evident from the siRNA and Myd88 studies, partial inhibition of MyD88 is sufficient to protect against Alu RNA. Localized intraocular therapy, the current standard of care in most retinal diseases, would further limit the likelihood of adverse infectious outcomes. It is reasonable to foresee development of MyD88 inhibitors for prevention or treatment of GA.

Example 2

Figure 13:
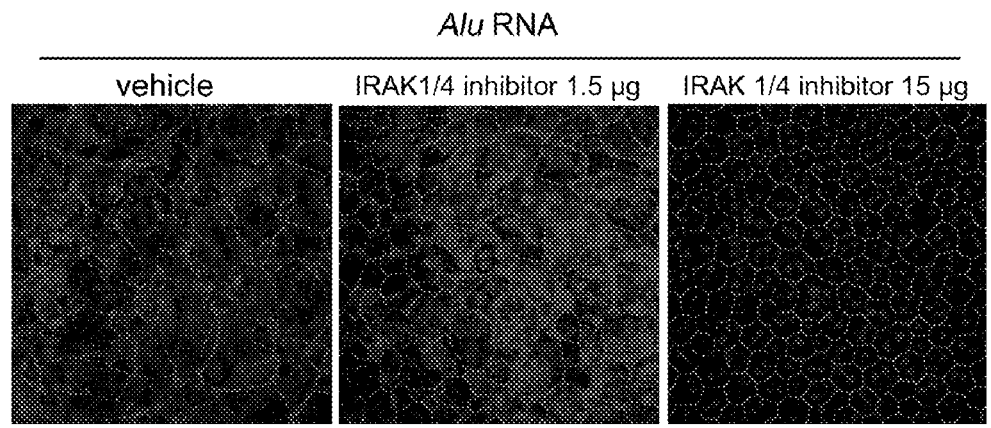
FIG. 13 includes a series of images showing stained flat mounts following intravitreous administration of N-(2-Morpholinylethyl)-2-(3-nitrobenzoylamido)-benzimidazole, an IRAK1/4 inhibitor, in wild-type mice, showing that IRAK1/4 inhibitors protects wild-type mice from Alu RNA-induced RPE degeneration in a dose-dependent manner.
Figure 14:
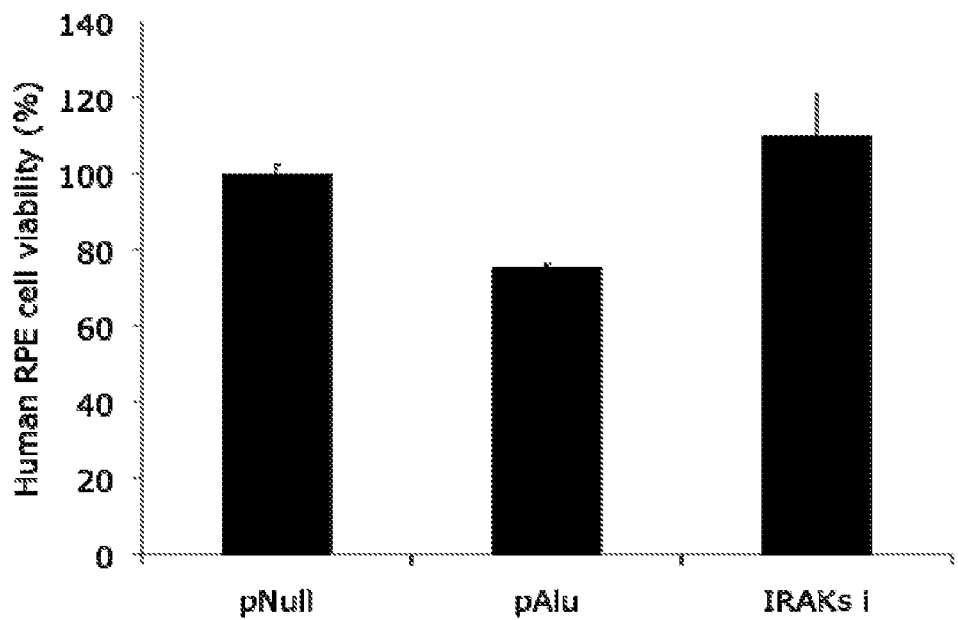
FIG. 14 is a bar graph presenting viability of human RPE cells, and showing that N-(2-Morpholinylethyl)-2-(3-nitrobenzoylamido)-benzimidazole, an IRAK1/4 inhibitor (100 µM), protects human RPE cells from pAlu-induced cytotoxicity.
Figure 15:
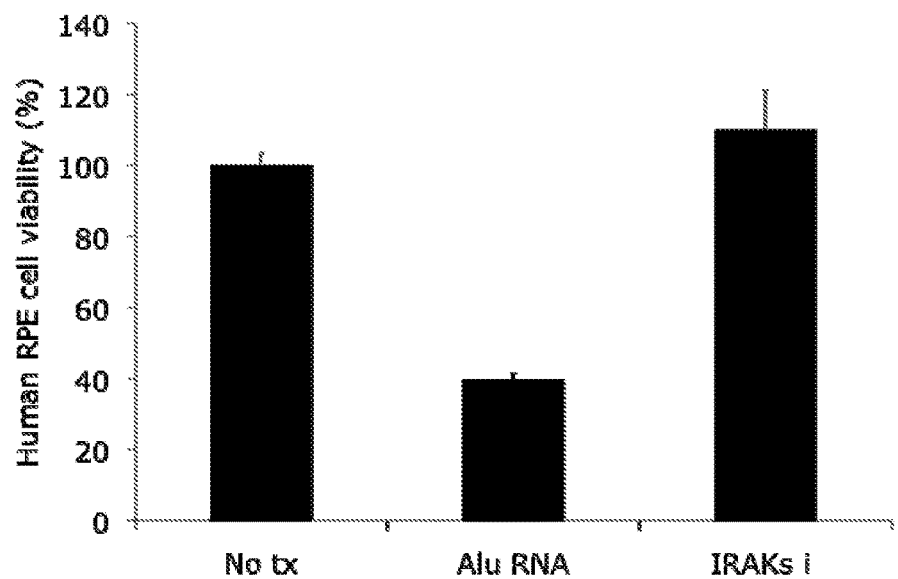
FIG. 15 is a bar graph presenting viability of human RPE cells, and showing that N-(2-Morpholinylethyl)-2-(3-nitrobenzoylamido)-benzimidazole, an IRAK1/4 inhibitor (100 µM), protects human RPE cells from Alu Alu-induced cytotoxicity.

It has been have shown that Alu RNA induces RPE degeneration via MyD88 signaling, and that Alu RNA increases phosphorylation of IRAK1 and IRAK4, kinases downstream of MyD88. To determine whether IRAK1/IRAK4 phosphorylation is critical to Alu RNA-induced RPE degeneration, N-(2-Morpholinylethyl)-2-(3-nitrobenzoylamido)-benzimidazole, an IRAK/4 inhibitor, was tested. Indeed it was found that this IRAK/4 inhibitor blocked Alu RNA-induced RPE degeneration in wild-type mice in a dose-dependent manner (FIG. 13). With reference to FIG. 13, Alu RNA was injected subretinally in wild-type mice to induce RPE degeneration. Compared to vehicle administration, intravitreous administration of an inhibitor of IRAK1/4 reduced the RPE degeneration induced by Alu RNA in a dose-dependent fashion (1.5-15 μg). With reference to FIG. 14, exposure of human RPE cells to an inhibitor of IRAK1/4 rescued the cell death induced by transfection of pAlu. With reference to FIG. 15, exposure of human RPE cells to an inhibitor of IRAK1/4 rescued the cell death induced by transfection of Alu RNA.

As noted herein, methods disclosed in the present application can be useful for treating all forms of macular degeneration, including the wet form of macular degeneration (e.g., angiogenesis/blood vessel growth). By way of specific example, a MyD88 inhibitor can be used to treat various forms of macular degeneration, and is specifically contemplated for inhibition of choroidal neovascularization.

Figure 16:
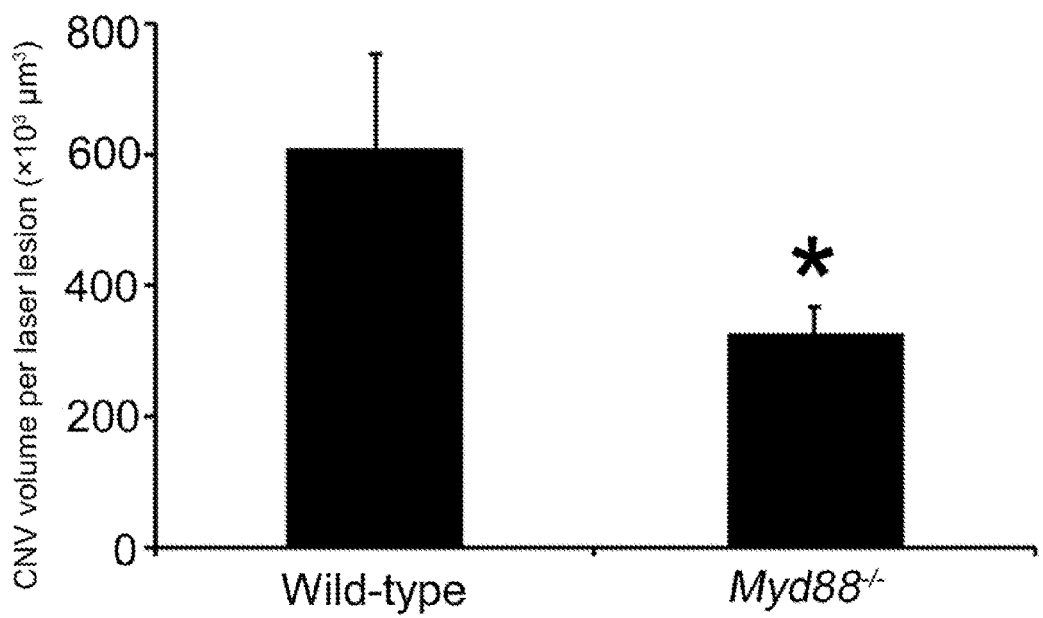
FIG. 16 is a bar graph showing that MyD88$^{-/-}$ mice have reduced laser-induced choroidal neovascularization as compared to wild-type mice.
Figure 17:
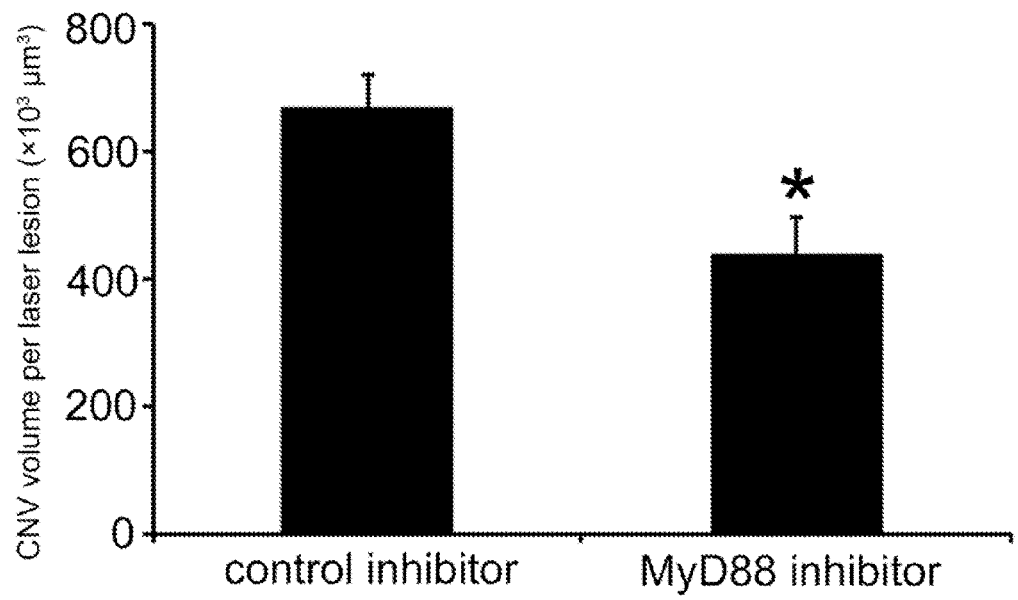
FIG. 17 is a bar graph showing that intravitreous injection of a peptide MyD88 inhibitor reduced laser-induced choroidal neovascularization in wild-type mice compared to a control peptide inhibitor.
Figure 18:
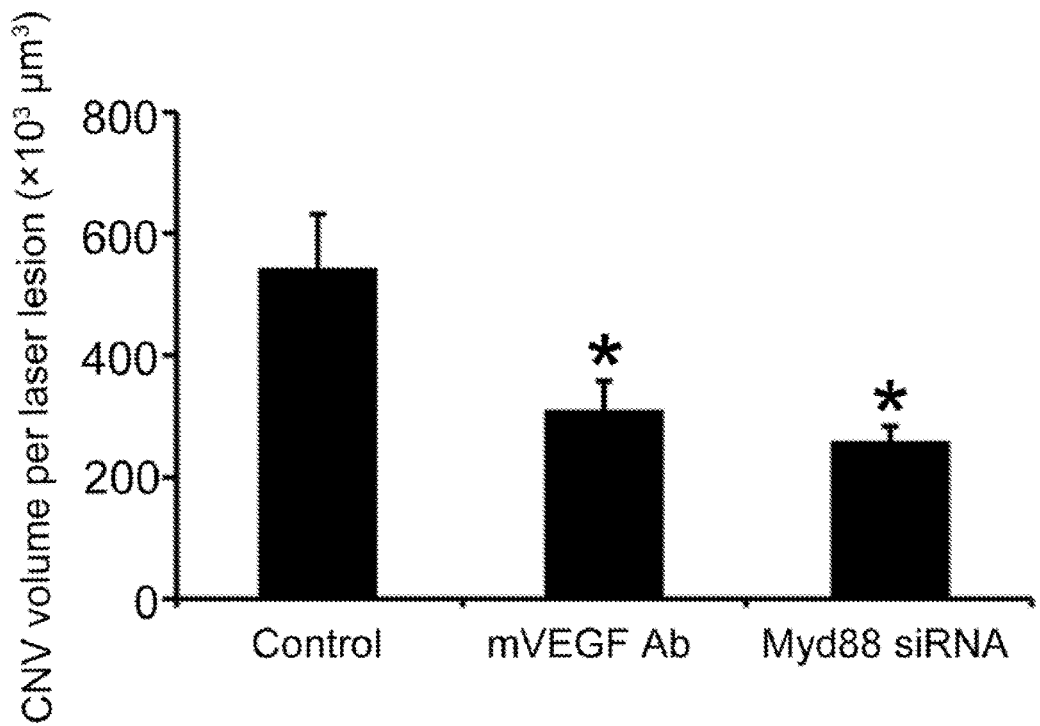
FIG. 18 is a bar graph showing that intravitreous injection of an siRNA targeting MyD88 (2 µg) reduced laser-induced choroidal neovascularization in wild-type mice at least as well as a neutralizing anti-mouse VEGF antibody, compared to a control sirRNA.

Relevant data are set forth in FIGS. 16-19. FIG. 16 is a bar graph showing that MyD88$^{-/-}$ mice have reduced laser-induced choroidal neovascularization as compared to wild-type mice. FIG. 17 is a bar graph showing that intravitreous injection of a peptide MyD88 inhibitor reduced laser-induced choroidal neovascularization in wild-type mice compared to a control peptide inhibitor. FIG. 18 is a bar graph showing that intravitreous injection of an siRNA targeting MyD88 (2 μg) reduced laser-induced choroidal neovascularization in wild-type mice at least as well as a neutralizing anti-mouse VEGF antibody, compared to a control sirRNA. FIG. 19 is a bar graph showing that intravitreous injection of an inhibitor of IRAK1/4 reduced laser-induced choroidal neovascularization in wild-type mice compared to vehicle.

Throughout this document, various references are mentioned. All such references are incorporated herein by reference, including the references set forth in the following list:

REFERENCES

Adachi, O., Kawai, T., Takeda, K., Matsumoto, M., Tsutsui, H., Sakagami, M., Nakanishi, K., and Akira, S. (1998). Targeted disruption of the MyD88 gene results in loss of IL-1- and IL-18-mediated function. Immunity 9, 143-150.

Akira, S., Uematsu, S., and Takeuchi, O. (2006). Pathogen recognition and innate immunity. Cell 124, 783-801.

Alexander, J. J., and Hauswirth, W. W. (2008). Adeno-associated viral vectors and the retina. Adv Exp Med Biol 613, 121-128

Alexopoulou, L., Holt, A. C., Medzhitov, R., and Flavell, R. A. (2001). Recognition of double-stranded RNA and activation of NF-kappaB by Toll-like receptor 3. Nature 413, 732-738.

Aliprantis, A. O., Yang, R. B., Weiss, D. S., Godowski, P., and Zychlinsky, A. (2000). The apoptotic signaling pathway activated by Toll-like receptor-2. EMBO J 19, 3325-3336.

Allensworth, J. J., Planck, S. R., Rosenbaum, J. T., and Rosenzweig, H. L. (2011). Investigation of the differential potentials of TLR agonists to elicit uveitis in mice. J Leukoc Biol.

Ambati, J., Ambati, B. K., Yoo, S. H., Ianchulev, S., and Adamis, A. P. (2003). Age-related macular degeneration: etiology, pathogenesis, and therapeutic strategies. Sury Ophthalmol 48, 257-293.

Batzer, M. A., and Deininger, P. L. (2002). Alu repeats and human genomic diversity. Nat Rev Genet 3, 370-379.

Bauernfeind, F., Bartok, E., Rieger, A., Franchi, L., Nunez, G., and Hornung, V. (2011). Cutting edge: reactive oxygen species inhibitors block priming, but not activation, of the NLRP3 inflammasome. J Immunol 187, 613-617.

Bauernfeind, F. G., Horvath, G., Stutz, A., et al. (2009). "Cutting edge: NF-kappaB activating pattern recognition and cytokine receptors license NLRP3 inflammasome activation by regulating NLRP3 expression." J Immunol 183(2): 787-791.

Bennett, E. A., Keller, H., Mills, R. E., Schmidt, S., Moran, J. V., Weichenrieder, O., and Devine, S. E. (2008). Active Alu retrotransposons in the human genome. Genome Res 18, 1875-1883

Bernstein, E., Caudy, A. A., Hammond, S. M., and Hannon, G. J. (2001). Role for a bidentate ribonuclease in the initiation step of RNA interference. Nature 409, 363-366.

Blaauwgeers, H. G., Holtkamp, G. M., Rutten, H., Witmer, A. N., Koolwijk, P., Partanen, T. A., Alitalo, K., Kroon, M. E., Kijlstra, A., van Hinsbergh, V. W., et al. (1999). Polarized vascular endothelial growth factor secretion by human retinal pigment epithelium and localization of vascular endothelial growth factor receptors on the inner choriocapillaris. Evidence for a trophic paracrine relation. Am J Pathol 155, 421-428.

Bogdanovich, S., McNally, E. M., and Khurana, T. S. (2008). Myostatin blockade improves function but not histopathology in a murine model of limb-girdle muscular dystrophy 2C. Muscle Nerve 37, 308-316.

Cao, Z., Henzel, W. J., and Gao, X. (1996). IRAK: a kinase associated with the interleukin-1 receptor. Science 271, 1128-1131.

Chandrasekar, B., Vemula, K., Surabhi, R. M., Li-Weber, M., Owen-Schaub, L. B., Jensen, L. E., and Mummidi, S. (2004). Activation of intrinsic and extrinsic proapoptotic signaling pathways in interleukin-18-mediated human cardiac endothelial cell death. J Biol Chem 279, 20221-20233.

Dhellin, O., Maestre, J., and Heidmann, T. (1997). Functional differences between the human LINE retrotransposon and retroviral reverse transcriptases for in vivo mRNA reverse transcription. EMBO J 16, 6590-6602.

Diebold, S. S., Kaisho, T., Hemmi, H., Akira, S., and Reis e Sousa, C. (2004). Innate antiviral responses by means of TLR7-mediated recognition of single-stranded RNA. Science 303, 1529-1531.

Dunaief, J. L., Dentchev, T., Ying, G. S., and Milam, A. H. (2002). The role of apoptosis in age-related macular degeneration. Arch Ophthalmol 120, 1435-1442.

Feldmeyer, L., Keller, M., Niklaus, G., Hohl, D., Werner, S., and Beer, H. D. (2007). The inflammasome mediates UVB-induced activation and secretion of interleukin-1beta by keratinocytes. Curr Biol 17, 1140-1145.

Fernandes-Alnemri, T., Wu, J., Yu, J. W., Datta, P., Miller, B., Jankowski, W., Rosenberg, S., Zhang, J., and Alnemri, E. S. (2007). The pyroptosome: a supramolecular assembly of ASC dimers mediating inflammatory cell death via caspase-1 activation. Cell Death Differ 14, 1590-1604.

Ferrara, N. (2010). Vascular endothelial growth factor and age-related macular degeneration: from basic science to therapy. Nat Med 16, 1107-1111.

Fink, S. L., Bergsbaken, T., and Cookson, B. T. (2008). Anthrax lethal toxin and *Salmonella* elicit the common cell death pathway of caspase-1-dependent pyroptosis via distinct mechanisms. Proc Natl Acad Sci USA 105, 4312-4317.

Fink, S. L., and Cookson, B. T. (2006). Caspase-1-dependent pore formation during pyroptosis leads to osmotic lysis of infected host macrophages. Cell Microbiol 8, 1812-1825.

Ghayur, T., Banerjee, S., Hugunin, M., Butler, D., Herzog, L., Carter, A., Quintal, L., Sekut, L., Talanian, R., Paskind, M., et al. (1997). Caspase-1 processes IFN-gamma-inducing factor and regulates LPS-induced IFN-gamma production. Nature 386, 619-623.

Gu, Y., Kuida, K., Tsutsui, H., Ku, G., Hsiao, K., Fleming, M. A., Hayashi, N., Higashino, K., Okamura, H., Nakanishi, K., et al. (1997). Activation of interferon-gamma inducing factor mediated by interleukin-1beta converting enzyme. Science 275, 206-209.

Guarda, G., Braun, M., Staehli, F., Tardivel, A., Mattmann, C., Forster, I., Farlik, M., Decker, T., Du Pasquier, R. A., Romero, P., et al. (2011). Type I interferon inhibits interleukin-1 production and inflammasome activation. Immunity 34, 213-223.

Guarda, G., Dostert, C., Staehli, F., Cabalzar, K., Castillo, R., Tardivel, A., Schneider, P., and Tschopp, J. (2009). T cells dampen innate immune responses through inhibition of NLRP1 and NLRP3 inflammasomes. Nature 460, 269-273.

Halle, A., Hornung, V., Petzold, G. C., Stewart, C. R., Monks, B. G., Reinheckel, T., Fitzgerald, K. A., Latz, E., Moore, K. J., and Golenbock, D. T. (2008). The NALP3 inflammasome is involved in the innate immune response to amyloid-beta. Nat Immunol 9, 857-865.

Heil, F., Hemmi, H., Hochrein, H., Ampenberger, F., Kirschning, C., Akira, S., Lipford, G., Wagner, H., and Bauer, S. (2004). Species-specific recognition of single-stranded RNA via toll-like receptor 7 and 8. Science 303, 1526-1529.

Hoebe, K., Du, X., Georgel, P., Janssen, E., Tabeta, K., Kim, S. O., Goode, J., Lin, P., Mann, N., Mudd, S., et al. (2003). Identification of Lps2 as a key transducer of MyD88-independent TIR signalling. Nature 424, 743-748.

Hornung, V., Ellegast, J., Kim, S., Brzozka, K., Jung, A., Kato, H., Poeck, H., Akira, S., Conzelmann, K. K., Schlee, M., et al. (2006). 5'-Triphosphate RNA is the ligand for RIG-I. Science 314, 994-997.

Kanakaraj, P., Ngo, K., Wu, Y., Angulo, A., Ghazal, P., Harris, C. A., Siekierka, J. J., Peterson, P. A., and Fung-Leung, W. P. (1999). Defective interleukin (IL)-18-mediated natural killer and T helper cell type 1 responses in IL-1 receptor-associated kinase (IRAK)-deficient mice. J Exp Med 189, 1129-1138.

Kaneko, H., Dridi, S., Tarallo, V., Gelfand, B. D., Fowler, B. J., Cho, W. G., Kleinman, M. E., Ponicsan, S. L., Hauswirth, W. W., Chiodo, V. A., et al. (2011). DICER1 deficit induces Alu RNA toxicity in age-related macular degeneration. Nature 471, 325-330.

Kanneganti, T. D., Ozoren, N., Body-Malapel, M., Amer, A., Park, J. H., Franchi, L., Whitfield, J., Barchet, W., Colonna, M., Vandenabeele, P., et al. (2006). Bacterial RNA and small antiviral compounds activate caspase-1 through cryopyrin/Nalp3. Nature 440, 233-236.

Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature 441, 101-105.

Keller, M., Ruegg, A., Werner, S., and Beer, H. D. (2008). Active caspase-1 is a regulator of unconventional protein secretion. Cell 132, 818-831.

Kleinman, M. E., Kaneko, H., Cho, W. G., Dridi, S., Fowler, B. J., Blandford, A. D., Albuquerque, R. J., Hirano, Y., Terasaki, H., Kondo, M., et al. (2011). Short-interfering RNAs Induce Retinal Degeneration via TLR3 and IRF3. Mol Ther.

Kleinman, M. E., Yamada, K., Takeda, A., Chandrasekaran, V., Nozaki, M., Baffi, J. Z., Albuquerque, R. J., Yamasaki, S., Itaya, M., Pan, Y., et al. (2008). Sequence- and target-independent angiogenesis suppression by siRNA via TLR3. Nature 452, 591-597.

Kumar, H., Kawai, T., Kato, H., Sato, S., Takahashi, K., Coban, C., Yamamoto, M., Uematsu, S., Ishii, K. J., Takeuchi, O., et al. (2006). Essential role of IPS-1 in innate immune responses against RNA viruses. J Exp Med 203, 1795-1803.

Kumar, M. V., Nagineni, C. N., Chin, M. S., Hooks, J. J., and Detrick, B. (2004). Innate immunity in the retina: Toll-like receptor (TLR) signaling in human retinal pigment epithelial cells. J Neuroimmunol 153, 7-15.

Lamkanfi, M., Mueller, J. L., Vitari, A. C., Misaghi, S., Fedorova, A., Deshayes, K., Lee, W. P., Hoffman, H. M., and Dixit, V. M. (2009). Glyburide inhibits the Cryopyrin/Nalp3 inflammasome. J Cell Biol 187, 61-70.

Lander, E. S., Linton, L. M., Birren, B., Nusbaum, C., Zody, M. C., Baldwin, J., Devon, K., Dewar, K., Doyle, M., FitzHugh, W., et al. (2001). Initial sequencing and analysis of the human genome. Nature 409, 860-921.

Loiarro, M., Sette, C., Gallo, G., Ciacci, A., Fanto, N., Mastroianni, D., Carminati, P., and Ruggiero, V. (2005). Peptide-mediated interference of TIR domain dimerization in MyD88 inhibits interleukin-1-dependent activation of NF-κB. J Biol Chem 280, 15809-15814.

Lopez, P. F., Sippy, B. D., Lambert, H. M., Thach, A. B., and Hinton, D. R. (1996). Transdifferentiated retinal pigment epithelial cells are immunoreactive for vascular endothelial growth factor in surgically excised age-related macular degeneration-related choroidal neovascular membranes. Invest Ophthalmol Vis Sci 37, 855-868.

Mariathasan, S., Newton, K., Monack, D. M., Vucic, D., French, D. M., Lee, W. P., Roose-Girma, M., Erickson, S., and Dixit, V. M. (2004). Differential activation of the inflammasome by caspase-1 adaptors ASC and Ipaf. Nature 430, 213-218.

Mariathasan, S., Weiss, D. S., Newton, K., McBride, J., O'Rourke, K., Roose-Girma, M., Lee, W. P., Weinrauch, Y., Monack, D. M., and Dixit, V. M. (2006). Cryopyrin activates the inflammasome in response to toxins and ATP. Nature 440, 228-232.

Maranon, F., Mayor, A., and Tschopp, J. (2009). The inflammasomes: guardians of the body. Annu Rev Immunol 27, 229-265.

Masters, S. L., Dunne, A., Subramanian, S. L., Hull, R. L., Tannahill, G. M., Sharp, F. A., Becker, C., Franchi, L., Yoshihara, E., Chen, Z., et al. (2010). Activation of the NLRP3 inflammasome by islet amyloid polypeptide provides a mechanism for enhanced IL-1beta in type 2 diabetes. Nat Immunol 11, 897-904.

McClure, M. A. (1991). Evolution of retroposons by acquisition or deletion of retrovirus-like genes. Mol Biol Evol 8, 835-856.

McLeod, D. S., Grebe, R., Bhutto, I., Merges, C., Baba, T., and Lutty, G. A. (2009). Relationship between RPE and choriocapillaris in age-related macular degeneration. Invest Ophthalmol Vis Sci 50, 4982-4991.

Miao, E. A., Leaf, I. A., Treuting, P. M., Mao, D. P., Dors, M., Sarkar, A., Warren, S. E., Wewers, M. D., and Aderem, A. (2010). Caspase-1-induced pyroptosis is an innate immune effector mechanism against intracellular bacteria. Nat Immunol 11, 1136-1142.

Muruve, D. A., Petrilli, V., Zaiss, A. K., White, L. R., Clark, S. A., Ross, P. J., Parks, R. J., and Tschopp, J. (2008). The inflammasome recognizes cytosolic microbial and host DNA and triggers an innate immune response. Nature 452, 103-107.

Muzio, M., Ni, J., Feng, P., and Dixit, V. M. (1997). IRAK (Pelle) family member IRAK-2 and MyD88 as proximal mediators of IL-1 signaling. Science 278, 1612-1615.

Nakahira, K., Haspel, J. A., Rathinam, V. A., Lee, S. J., Dolinay, T., Lam, H. C., Englert, J. A., Rabinovitch, M., Cernadas, M., Kim, H. P., et al. (2011). Autophagy proteins regulate innate immune responses by inhibiting the release of mitochondrial DNA mediated by the NALP3 inflammasome. Nat Immunol 12, 222-230.

Ngo, V. N., Young, R. M., Schmitz, R., Jhavar, S., Xiao, W., Lim, K. H., Kohlhammer, H., Xu, W., Yang, Y., Zhao, H., et al. (2011). Oncogenically active MYD88 mutations in human lymphoma. Nature 470, 115-119.

O'Neill, L. A., and Bowie, A. G. (2007). The family of five: TIR-domain-containing adaptors in Toll-like receptor signalling. Nat Rev Immunol 7, 353-364.

Ohtsuki, T., Micallef, M. J., Kohno, K., Tanimoto, T., Ikeda, M., and Kurimoto, M. (1997). Interleukin 18 enhances Fas ligand expression and induces apoptosis in Fas-expressing human myelomonocytic KG-1 cells. Anticancer Res 17, 3253-3258.

Parker, J. S., Roe, S. M., and Barford, D. (2004). Crystal structure of a PIWI protein suggests mechanisms for siRNA recognition and slicer activity. EMBO J 23, 4727-4737.

Picard, C., von Bernuth, H., Ghandil, P., Chrabieh, M., Levy, O., Arkwright, P. D., McDonald, D., Geha, R. S., Takada, H., Krause, J. C., et al. (2010). Clinical features and outcome of patients with IRAK-4 and MyD88 deficiency. Medicine (Baltimore) 89, 403-425.

Pichlmair, A., Lassnig, C., Eberle, C. A., Goma, M. W., Baumann, C. L., Burkard, T. R., Burckstummer, T., Stefanovic, A., Krieger, S., Bennett, K. L., et al. (2011). IFIT1 is an antiviral protein that recognizes 5'-triphosphate RNA. Nat Immunol 12, 624-630.

Puente, X. S., Pinyol, M., Quesada, V., Conde, L., Ordonez, G. R., Villamor, N., Escaramis, G., Jares, P., Bea, S., Gonzalez-Diaz, M., et al. (2011). Whole-genome sequencing identifies recurrent mutations in chronic lymphocytic leukaemia. Nature 475, 101-105.

Qiao, Y., Wang, P., Qi, J., et al. (2012). "TLR-induced NF-kappaB activation regulates NLRP3 expression in murine macrophages." FEBS Lett 586(7): 1022-1026.

Qureshi, N., Takayama, K., and Kurtz, R. (1991). Diphosphoryl lipid A obtained from the nontoxic lipopolysaccharide of *Rhodopseudomonas sphaeroides* is an endotoxin antagonist in mice. Infect Immun 59, 441-444.

Rakoff-Nahoum, S., and Medzhitov, R. (2007). Regulation of spontaneous intestinal tumorigenesis through the adaptor protein MyD88. Science 317, 124-127.

Reuter, M., Benninger, P., Chuma, S., Shah, H., Hosokawa, M., Funaya, C., Antony, C., Sachidanandam, R., and Pillai, R. S. (2011). Miwi catalysis is required for piRNA amplification-independent LINE1 transposon silencing. Nature.

Saitoh, T., Fujita, N., Jang, M. H., Uematsu, S., Yang, B. G., Satoh, T., Omori, H., Noda, T., Yamamoto, N., Komatsu, M., et al. (2008). Loss of the autophagy protein Atg16L1 enhances endotoxin-induced IL-1beta production. Nature 456, 264-268.

Schroder, K., and Tschopp, J. (2010). The inflammasomes. Cell 140, 821-832.

Schroder, K., Zhou, R., and Tschopp, J. (2010). The NLRP3 inflammasome: a sensor for metabolic danger? Science 327, 296-300.

Shaikh, T. H., Roy, A. M., Kim, J., Batzer, M. A., and Deininger, P. L. (1997). cDNAs derived from primary and small cytoplasmic Alu (scAlu) transcripts. J Mol Biol 271, 222-234.

Smith, W., Assink, J., Klein, R., Mitchell, P., Klaver, C. C., Klein, B. E., Hofman, A., Jensen, S., Wang, J. J., and de Jong, P. T. (2001). Risk factors for age-related macular degeneration: Pooled findings from three continents. Ophthalmology 108, 697-704.

Stennicke, H. R., Jurgensmeier, J. M., Shin, H., et al. (1998). "Pro-caspase-3 is a major physiologic target of caspase-8." J Biol Chem 273(42): 27084-27090.

Streilein, J. W. (2003). Ocular immune privilege: therapeutic opportunities from an experiment of nature. Nat Rev Immunol 3, 879-889.

Sun, D., and Ding, A. (2006). MyD88-mediated stabilization of interferon-gamma-induced cytokine and chemokine mRNA. Nat Immunol 7, 375-381.

Sun, Q., Sun, L., Liu, H. H., Chen, X., Seth, R. B., Forman, J., and Chen, Z. J. (2006). The specific and essential role of MAVS in antiviral innate immune responses. Immunity 24, 633-642.

Suzuki, N., Chen, N. J., Millar, D. G., Suzuki, S., Horacek, T., Hara, H., Bouchard, D., Nakanishi, K., Penninger, J. M., Ohashi, P. S., et al. (2003). IL-1 receptor-associated kinase 4 is essential for IL-18-mediated NK and Th1 cell responses. J Immunol 170, 4031-4035.

Suzuki, N., Suzuki, S., Duncan, G. S., Millar, D. G., Wada, T., Mirtsos, C., Takada, H., Wakeham, A., Itie, A., Li, S., et al. (2002). Severe impairment of interleukin-1 and Toll-like receptor signalling in mice lacking IRAK-4. Nature 416, 750-756.

Tabeta, K., Hoebe, K., Janssen, E. M., Du, X., Georgel, P., Crozat, K., Mudd, S., Mann, N., Sovath, S., Goode, J., et al. (2006). The Unc93b1 mutation 3d disrupts exogenous antigen presentation and signaling via Toll-like receptors 3, 7 and 9. Nat Immunol 7, 156-164.

Takeda, A., Baffi, J. Z., Kleinman, M. E., Cho, W. G., Nozaki, M., Yamada, K., Kaneko, H., Albuquerque, R. J., Dridi, S., Saito, K., et al. (2009). CCR3 is a target for age-related macular degeneration diagnosis and therapy. Nature 460, 225-230.

Thornberry, N. A., Bull, H. G., Calaycay, J. R., Chapman, K. T., Howard, A. D., Kostura, M. J., Miller, D. K., Molineaux, S. M., Weidner, J. R., Aunins, J., et al. (1992). A novel heterodimeric cysteine protease is required for interleukin-1 beta processing in monocytes. Nature 356, 768-774.

Tschopp, J., Maranon, F., and Burns, K. (2003). NALPs: a novel protein family involved in inflammation. Nat Rev Mol Cell Biol 4, 95-104.

Vandanmagsar, B., Youm, Y. H., Ravussin, A., Galgani, J. E., Stadler, K., Mynatt, R. L., Ravussin, E., Stephens, J. M., and Dixit, V. D. (2011). The NLRP3 inflammasome instigates obesity-induced inflammation and insulin resistance. Nat Med 17, 179-188.

Vandenabeele, P., Vanden Berghe, T., and Festjens, N. (2006). Caspase inhibitors promote alternative cell death pathways. Sci STKE 2006, pe44.

Verhoef, P. A., Kertesy, S. B., Lundberg, K., Kahlenberg, J. M., and Dubyak, G. R. (2005). Inhibitory effects of chloride on the activation of caspase-1, IL-1beta secretion, and cytolysis by the P2X7 receptor. J Immunol 175, 7623-7634.

Vogt, S. D., Curcio, C. A., Wang, L., Li, C. M., McGwin, G., Jr., Medeiros, N. E., Philp, N. J., Kimble, J. A., and Read, R. W. (2011). Retinal pigment epithelial expression of complement regulator CD46 is altered early in the course of geographic atrophy. Exp Eye Res.

von Bernuth, H., Picard, C., Jin, Z., Pankla, R., Xiao, H., Ku, C. L., Chrabieh, M., Mustapha, I. B., Ghandil, P., Camcioglu, Y., et al. (2008). Pyogenic bacterial infections in humans with MyD88 deficiency. Science 321, 691-696.

Wen, H., Orris, D., Lei, Y., Jha, S., Zhang, L., Huang, M. T., Brickey, W. J., and Ting, J. P. (2011). Fatty acid-induced NLRP3-ASC inflammasome activation interferes with insulin signaling. Nat Immunol 12, 408-415.

Yamamoto, M., Sato, S., Hemmi, H., Hoshino, K., Kaisho, T., Sanjo, H., Takeuchi, O., Sugiyama, M., Okabe, M., Takeda, K., et al. (2003). Role of adaptor TRIF in the MyD88-independent toll-like receptor signaling pathway. Science 301, 640-643.

Yang, P., Tyrrell, J., Han, I., and Jaffe, G. J. (2009). Expression and modulation of RPE cell membrane complement regulatory proteins. Invest Ophthalmol Vis Sci 50, 3473-3481.

Yang, Y. L., Reis, L. F., Pavlovic, J., Aguzzi, A., Schafer, R., Kumar, A., Williams, B. R., Aguet, M., and Weissmann, C. (1995). Deficient signaling in mice devoid of double-stranded RNA-dependent protein kinase. EMBO J 14, 6095-6106.

Yang, Z., Stratton, C., Francis, P. J., Kleinman, M. E., Tan, P. L., Gibbs, D., Tong, Z., Chen, H., Constantine, R., Yang, X., et al. (2008). Toll-like receptor 3 and geographic atrophy in age-related macular degeneration. N Engl J Med 359, 1456-1463.

Zaki, M. H., Boyd, K. L., Vogel, P., Kastan, M. B., Lamkanfi, M., and Kanneganti, T. D. (2010). The NLRP3 inflammasome protects against loss of epithelial integrity and mortality during experimental colitis. Immunity 32, 379-391.

What is claimed is:

1. A method of treating dry macular degeneration, comprising:
    (a) identifying a subject in need of treatment for dry macular degeneration; and
    (b) administering a composition to the subject the composition binding with MyD88 in an retinal pigmented epithelium (RPE) cell of the subject to inhibit the MyD88; with IL-18 in an RPE cell of the subject to inhibit the IL-18; or with NLRP3 inflammasome, or Caspase-1 in an RPE cell of the subject to inhibit the inflammasome.

2. The method of claim 1, wherein the composition comprises MyD88 siRNA.

* * * * *